United States Patent [19]
Paoletti et al.

[11] Patent Number: 5,891,442
[45] Date of Patent: *Apr. 6, 1999

[54] INFECTIOUS BURSAL DISEASE VIRUS RECOMBINATION POXVIRUS VACCINE

[75] Inventors: Enzo Paoletti, Delmar; Jill Taylor, Albany; Russell Gettig, Averill Park, all of N.Y.

[73] Assignee: Virogenetics Corporation, Troy, N.Y.

[ * ] Notice: The term of this patent shall not extend beyond the expiration date of Pat. Nos. 5,641,490 and 5,658,572.

[21] Appl. No.: 480,697

[22] Filed: Jun. 7, 1995

Related U.S. Application Data

[62] Division of Ser. No. 303,124, Sep. 7, 1994, Pat. No. 5,641,490, which is a continuation of Ser. No. 918,311, Jul. 21, 1992, abandoned, which is a continuation-in-part of Ser. No. 736,254, Jul. 26, 1991, abandoned.

[51] Int. Cl.$^6$ .......................... A61K 39/12; C12P 21/06; C12N 15/00; C07H 21/02
[52] U.S. Cl. ...................................... 424/199.1; 424/204.1; 424/232.1; 435/69.1; 435/69.3; 435/172.3; 435/235.1; 435/240.1; 435/320.1; 536/23.1; 536/23.72; 935/65; 935/9; 935/32; 935/57
[58] Field of Search .................................. 435/69.1, 69.3, 435/172.3, 235.1, 240.1, 320.1; 424/199.1, 204.1, 232.1; 536/23.1, 23.72; 935/65, 9, 32, 57

[56] References Cited

PUBLICATIONS

Jagadish, M. et al 1988, *J. Virol.* vol. 62, No. 3, pp. 1084–1087.
Jagadish, M. et al 1991, *Virology* vol. 184, pp. 805–807.
Azad, A. et al 1986, *Virology* vol. 149, pp. 190–198.
Fahey, K. et al 1989, *J. Gen. Virology*, vol. 70, pp. 1473–1481.
Azad, A. et al., 1987, Virology–vol. 161, pp. 145–152.
Bayliss, C. et al., 1990, J. Gen. Virol., vol. 71, pp. 1303–1312.
Taylor, J. et al, 1988, Vaccine, vol. 6, pp. 504–508.
Taylor, J. et al, 1990, J. of Virol., pp. 1441–1450.
Kibenge, F. et al, 1988, J. Gen. Virol, vol. 69, pp. 1757–1775.

*Primary Examiner*—Marian C. Knode
*Assistant Examiner*—Ali R. Salimi
*Attorney, Agent, or Firm*—McDonnell Boehnen Hulbert & Berghoff

[57] ABSTRACT

What is described is a recombinant poxvirus, such as fowlpox virus, containing foreign DNA from infectious bursal disease virus. What is also described is a vaccine containing the recombinant poxvirus for inducing an immunological response in a host animal inoculated with the vaccine.

40 Claims, 4 Drawing Sheets

FIG. 1A

```
         10        20        30        40        50        60        70        80        90       100
GATATCTGTGGTCTATATATACTACACCCTACGATATTAACCAACGAGTTTCTCACAAGAAAACTTGTTTAGTAGATAGAGATTCTTGATTGTGTTTA
        110       120       130       140       150       160       170       180       190       200
AAAGAAGTACCAGTAAAAAGTGGCATATGCATAGAAGAAATAAACAAAAAACATATTTCCGAACAGTATTTGGAATTCTCCCAAGTTGTAAACATAT
        210       220       230       240       250       260       270       280       290       300
TTTTTGCCTATCATGTATAAGACGTTGGGCAGATACTACCAGAAATACAGAGATACTGAAAATACGTGTCCTGAATGTAGAATAGTTTTTCCTTTCATAATA
        310       320       330       340       350       360       370       380       390       400
CCCAGTAGGTATTGGATAGATAATAAATATGATAAAAAATATTATATAATAGATATAAGAAAATGATTTTTACAAAAATAACCTATAAGAACAATAAAA
        410       420       430       440       450       460       470       480       490       500
ATATAATTACATTTACGGAAAATAGCTGGTTTTAGTTTTACCAACTTAGAGTAATTATCATATTGAATCTATATTGTTTTTAGTTATATAAAAACATGAT
        510       520       530       540       550       560       570       580       590       600
TAGCCCCCAATCGGATGAAAATATAAAAGATGTTGAGAATTTCGAATACAACAAAAAGAGGAATCGTACGTTGTCCATATCCAAACATATAAATAAAAAT
        610       620       630       640       650       660       670       680       690       700
TCAAAAGTAGTATTATACTGGATGTTTAGAGATCAACGTGTACAAGATAATAATTGGGCTTTAATTTACGCACAACGATTAGCGTTAAAACTCAAAATACCTC
        710       720       730       740       750       760       770       780       790       800
TAAGAATATGCTTTTGTGTCGTGCCAAATTTCACACTACTTCTAGACACTTTATGTTTTTTAATATCCGGTCTTAAGAAGTCGCGGAAGAATGTA
        810       820       830       840       850       860       870       880       890       900
AAAGACTATGTATAGGGTTTTCATTGATATATGGCGTACCAAAAGTAATAATTCCGTGTATAGTAAAAAAATACAGAGTCGGAGTAATCATAACGGATTT
        910       920       930       940       950       960       970       980       990      1000
CTTTCCATTACGTGTTCCCGAAAGATTAATGAAACAGACTGTAATATCTCTTCCAGATAACATACCTTTTATACAAGTAGACGCTCATATATAGTACCT
       1010      1020      1030      1040      1050      1060      1070      1080      1090      1100
TGTTGGGAAGCTTCTGATAAAGAAGAATACGGTGCACGAACTTTAAGAAAAAAGATATTTGATAAATTATATGAATATGACAGAATTTCCTGTTGTTC
       1110      1120      1130      1140      1150      1160      1170      1180      1190      1200
GTAAACATCCATACGGTCCATTTTCTATATCTATTGCAAAACCCAAAATATATCATTAGACAAGACGGTATTACCCGTAAAATGGGCAACGCCTGGAAC
       1210      1220      1230      1240      1250      1260      1270      1280      1290      1300
AAAAGCTGGAATAATTGTTTTAAAAGAATTTATAAAAAACAGATTACCGTCATACGACGCGGATCATAACAATCCTACGTGTGACGCTTTGAGTAACTTA
```

```
          1310          1320          1330          1340          1350          1360          1370          1380          1390          1400
TCTCCGTGGCTACATTTGGTCATGTATCCGCACAACGTGTTGCCTTAGAAGTATTAAAATGTATACGAGAAAGCAAAAAAACGTTGAAACGTTTATAG 1410          1420          1430          1440          1450          1460          1470          1480          1490          1500
ATGAAATAATTGTAAGAAGAACTATCGGATAATTTTTGTTACTATAACAAACATTATGATAGTATCCAGTCTACTCATTCATGGGTTAGAAAAACATT 1510          1520          1530          1540          1550          1560          1570          1580          1590          1600
AGAAGATCACATTAATGATCCTAGAAAGTATATATATTCCATTAAACAACTCGAAAAAGCGGAAACTCATGATCCTCTATGGACGCGTCACAAATGCAG 1610          1620          1630          1640          1650          1660          1670          1680          1690          1700
ATGGTGAGAGAAGGAAAAATGCATAGTTTTTTACGAATGTATTGGGCTAAGAAGATACTTGAATGGACTAGAACACCTGAAGACGCTTTGAGTTATAGTA 1710          1720          1730          1740          1750          1760          1770          1780          1790          1800
TCTATTTGAACAACAAGTACGAACTAGACGGCACGGATCCTAACGGATACGTAGGTTGTATGTGGTCTATTTGCGGATTACACGATAGAGCGTGGAAAGC 1810          1820          1830          1840          1850          1860          1870          1880          1890          1900
AAGACCGATATTTGGAAAGATAAGATATATGAATTATGAGAGTTCTAAGAGAAATTTGATGTTGCTGTATTTATACAGAAATAACAATTAAGATAAATAA 1910          1920          1930          1940          1950          1960          1970          1980          1990          2000
TATACAGCATTGTAACCATCGTCATCCGTTATACGGGGAATAATATTACCATACAGTATTATTAAATTTCTTACGAAGAATATAGATCGGTATTTATCG 2010          2020          2030          2040          2050          2060          2070          2080          2090          2100
TTAGTTTATTTTACATTTATTAATTAATGCTACTAGATTATGTGAATTACGAGGAATGACAAATTTAGTTATATAATTTATGATAAAATTAAGATAATAAT 2110          2120          2130          2140          2150          2160          2170          2180          2190          2200
AATGAAATCAAATAATTATGTAAATGCTACTAGATTATGTGAATTACGAGGAAGAAAGTTTACGAACTGGAAAAATTAAGTGAATCTAAAATATTAGTC 2210          2220          2230          2240          2250          2260          2270          2280          2290          2300
GATAATGTAAAAAAAATAAAATGATAAAACTAACCAGTTAAAAACGGATATATCGTTAAGGATATGATCATAAAGGAAGAGATACTTGCGGTT 2310          2320          2330          2340          2350          2360          2370          2380          2390          2400
ACTATGTACACCAAGATCTGGTATCTTCTATATCAAATTGGATATCTCCGTTATTCGCCGTTAAGGTAAATAAAATTATTAACTATTATATGTAATGA 2410          2420          2430          2440          2450          2460          2470          2480          2490          2500
ATATGATATACGACTTAGGCGAAATGGAATCTGATATGACAGAAGTAGTTGATAAATTAGTAGGAGGATAACAATGATGAAATAGCAGAAATA
```

FIG. 1B

```
     2510       2520       2530       2540       2550       2560       2570       2580       2590       2600
ATATATTTGTTAATAAATTTATAGAAAAATAAATTATAGCTAACATATCGTTATCAACTGAATTATCTAGTATATTAAATAATTTATAAATTTTATAAATT 2610       2620       2630       2640       2650       2660       2670       2680       2690       2700
TTAATAAAAATACAATAACGACATAAAGATATTTAATCTTTAATTCTTGAAAAACACATCTATAAACTAGATAAAAAGTTATTCGATAAAGAT 2710       2720       2730       2740       2750       2760       2770       2780       2790       2800
AATAATGAATCGAACGATGAAGAAAAATTGGAAACAGAAGTTGATAAGCTAATTTTTTCATCTAAATAGTATTATTTTATTGAAGTACGAAGTTTTACGTTA 2810       2820       2830       2840       2850       2860       2870       2880       2890       2900
GATAAATAATAAAGGTCGATTTTTACTTTGTTAAATATCAAATATGTCATTATCTGATAAAGATACAAAAACACACGGTGATTATCAACCATCTAACGAA 2910       2920       2930       2940       2950       2960       2970       2980       2990       3000
CAGATATTACAAAAAATACGTCGGACTATGGAAAACGAAGCTGATAGCCCTCAATAGAGAAGCATTAAAGAAATTGTTGTAGATGTTATGAAGAATTGGG 3010       3020       3030       3040       3050       3060       3070       3080       3090       3100
ATCATCCTCAACGAAGAATAGATAAGTTCTAAACTGGAAAAATGATACATTAAACGATTTAGATCATCTAAATACAGATGATAATATTAAGGAAATCA 3110       3120       3130       3140       3150       3160       3170       3180       3190       3200
TACAATGTCTGATTAGAGAATTTGCGTTTAAAAAGATCAATTCTATTATGTATAGTTATGCTATGGTAAAACTCAATTCAGATAACGAACATTGAAAGAT 3210       3220       3230       3240       3250       3260       3270       3280       3290       3300
AAAATTAAGGATTATTTTATAGAAACTATTCTTAAAGACAAACGTGGTTATAAACAAAAGCCATTACCCGGATTGGAAACTAAAATACTAGATAGTATTA 3310       3320       3330       3340       3350       3360       3370       3380       3390       3400
TAAGATTTAAAAAACATAAATTAATAGGTTTTTATAGATTGACTTATTATTATACAATATGGATAAAGATATATCAACTAGAAAGTTGAATGACGGA 3410       3420       3430       3440       3450       3460       3470       3480       3490       3500
TTCTTAATTTTATATTATGATTCAATAGAATCATTTGAGAAATAATATTGTGTAATCATTTTATAAATATCAGCGTTACTAGCTAAGAAAAACAAGGACTTTA 3510       3520       3530       3540       3550       3560       3570       3580       3590       3600
ATGAATGGCTAAAGATAGAATCATTTGAGAGAATAATAGAACTTTAGATAAAATTAATTACGATCTAGGACAACGATATTGTGAAGAACTTACGGCGCA 3610       3620       3630       3640       3650       3660
TCACATTCCAGTGTAATTATTGAGGTCAAAGCTAGTAACTTAATAGATGACAGGACAGCTG
```

*FIG. 1C*

```
   1 GATATCTGTG GTCTATATAT ACTACACCCT ACCGATATTA ACCAACGAGT TTCTCACAAG
  61 AAAACTTGTT TAGTAGATAG AGATTCTTTG ATTGTGTTTA AAAGAAGTAC CAGTAAAAAG
 121 TGTGGCATAT GCATAGAAGA AATAAACAAA AAACATATTT CCGAACAGTA TTTTGGAATT
 181 CTCCCAAGTT GTAAACATAT TTTTTGCCTA TCATGTATAA GACGTTGGGC AGATACTACC
 241 AGAAATACAG ATACTGAAAA TACGTGTCCT GAATGTAGAA TAGTTTTTCC TTTCATAATA
 301 CCCAGTAGGT ATTGGATAGA TAATAAATAT GATAAAAAAA TATTATATAA TAGATATAAG
 361 AAAATGATTT TTACAAAAAT ACCTATAAGA ACAATAAAAA TATAATTACA TTTACGGAAA
 421 ATAGCTGGTT TTAGTTTACC AACTTAGAGT AATTATCATA TTGAATCTAT ATTGTTTTTT
 481 AGTTATATAA AAACATGATT AGCCCCCAAT CGGATGAAAA TATAAAAGAT GTTGAGAATT
 541 TCGAATACAA CAAAAAGAGG AATCGTACGT TGTCCATATC CAAACATATA AATAAAAATT
 601 CAAAAGTAGT ATTATACTGG ATGTTTAGAG ATCAACGTGT ACAAGATAAT TGGGCTTTAA
 661 TTTACGCACA ACGATTAGCG TTAAAACTCA AAATACCTCT AAGAATATGC TTTTGTGTCG
 721 TGCCAAAATT TCACACTACT ACTTCTAGAC ACTTTATGTT TTTAATATCC GGTCTTAAAG
 781 AAGTCGCGGA AGAATGTAAA AGACTATGTA TAGGGTTTTC ATTGATATAT GGCGTACCAA
 841 AAGTAATAAT TCCGTGTATA GTAAAAAAAT ACAGAGTCGG AGTAATCATA ACGGATTTCT
 901 TTCCATTACG TGTTCCCGAA AGATTAATGA AACAGACTGT AATATCTCTT CCAGATAACA
 961 TACCTTTTAT ACAAGTAGAC GCTCATAATA TAGTACCTTG TTGGGAAGCT TCTGATAAAG
1021 AAGAATACGG TGCACGAACT TTAAGAAAAA AGATATTTGA TAAATTATAT GAATATATGA
1081 CAGAATTTCC TGTTGTTCGT AAACATCCAT ACGGTCCATT TTCTATATCT ATTGCAAAAC
1141 CCAAAAAATAT ATCATTAGAC AAGACGGTAT TACCCGTAAA ATGGGCAACG CCTGGAACAA
1201 AAGCTGGAAT AATTGTTTTA AAAGAATTTA TAAAAAACAG ATTACCGTCA TACGACGCGG
1261 ATCATAACAA TCCTACGTGT GACGCTTTGA GTAACTTATC TCCGTGGCTA CATTTTGGTC
1321 ATGTATCCGC ACAACGTGTT GCCTTAGAAG TATTAAAATG TATACGAGAA AGCAAAAAAA
1381 ACGTTGAAAC GTTTATAGAT GAAATAATTG TAAGAAGAGA ACTATCGGAT AATTTTTGTT
1441 ACTATAACAA ACATTATGAT AGTATCCAGT CTACTCATTC ATGGGTTAGA AAAACATTAG
1501 AAGATACAT TAATGATCCT AGAAAGTATA TATATTCCAT TAAACAACTC GAAAAAGCGG
1561 AAACTCATGA TCCTCTATGG AACGCGTCAC AAATGCAGAT GGTGAGAGAA GGAAAAATGC
1621 ATAGTTTTTT ACGAATGTAT TGGGCTAAGA AGATACTTGA ATGGACTAGA ACACCTGAAG
1681 ACGCTTTGAG TTATAGTATC TATTTGAACA ACAAGTACGA ACTAGACGGC ACGGATCCTA
1741 ACGGATACGT AGGTTGTATG TGGTCTATTT GCGGATTACA CGATAGAGCG TGGAAAGCAA
1801 GACCGATATT TGGAAAGATA AGATATATGA ATTATGAGAG TTCTAAGAAG AAATTTGATG
1861 TTGCTGTATT TATACAGAAA TACAATTAAG ATAAATAATA TACAGCATTG TAACCATCGT
1921 CATCCGTTAT ACGGGGAATA ATATTACCAT ACAGTATTAT TAAATTTTCT TACGAAGAAT
1981 ATAGATCGGT ATTTATCGTT AGTTTATTTT ACATTTATTA ATTAAACATG TCTACTATTA
2041 CCTGTTATGG AAATGACAAA TTTAGTTATA TAATTTATGA TAAAATTAAG ATAATAATAA
2101 TGAAATCAAA TAATTATGTA AATGCTACTA GATTATGTGA ATTACGAGGA AGAAAGTTTA
2161 CGAACTGGAA AAAATTAAGT GAATCTAAAA TATTAGTCGA TAATGTAAAA AAAATAAATG
2221 ATAAAACTAA CCAGTTAAAA ACGGATATGA TTATATACGT TAAGGATATT GATCATAAAG
2281 GAAGAGATAC TTGCGGTTAC TATGTACACC AAGATCTGGT ATCTTCTATA TCAAATTGGA
2341 TATCTCCGTT ATTCGCCGTT AAGGTAAATA AAATTATTAA CTATTATATA TGTAATGAAT
2401 ATGATATACG ACTTAGCGAA ATGGAATCTG ATATGACAGA AGTAATAGAT GTAGTTGATA
2461 AATTAGTAGG AGGATACAAT GATGAAATAG CAGAAATAAT ATATTTGTTT AATAAATTTA
2521 TAGAAAAATA TATTGCTAAC ATATCGTTAT CAACTGAATT ATCTAGTATA TTAAATAATT
2581 TTATAAATTT TATAAATTTT AATAAAAAAT ACAATAACGA CATAAAGATA TTTAATCTTT
2641 AATTCTTGAT CTGAAAAACA CATCTATAAA ACTAGATAAA AAGTTATCG ATAAAGATAA
2701 TAATGAATCG AACGATGAAA AATTGGAAAC AGAAGTTGAT AAGCTAATTT TTTTCATCTA
2761 AATAGTATTA TTTTATTGAA GTACGAAGTT TTACGTTAGA TAAATAATAA AGGTCGATTT
2821 TTACTTTGTT AAATATCAAA TATGTCATTA TCTGATAAAG ATACAAAAAC ACACGGTGAT
2881 TATCAACCAT CTAACGAACA GATATTACAA AAAATACGTC GGACTATGGA AAACGAAGCT
2941 GATAGCCTCA ATAGAAGAAG CATTAAAGAA ATTGTTGTAG ATGTTATGAA GAATTGGGAT
3001 CATCCTCAAC GAAGAAATAG ATAAAGTTCT AAACTGGAAA AATGATACAT TAAACGATTT
3061 AGATCATCTA AATACAGATG ATAATATTAA GGAAATCATA CAATGTCTGA TTAGAGAATT
3121 TGCGTTTAAA AAGATCAATT CTATTATGTA TAGTTATGCT ATGGTAAAAC TCAATTCAGA
3181 TAACGAACAT TGAAAGATAA AATTAAGGAT TATTTTATAG AAACTATTCT TAAAGACAAA
3241 CGTGGTTATA AACAAAAGCC ATTACCCGGA TTGGAAACTA AAATACTAGA TAGTATTATA
3301 AGATTTTAAA AACATAAAAT TAATAGGTTT TTATAGATTG ACTTATTATA TACAATATGG
3361 ATAAAAGATA TATATCAACT AGAAAGTTGA ATGACGGATT CTTAATTTTA TATTATGATT
3421 CAATAGAAAT TATTGTCATG TCGTGTAATC ATTTTATAAA TATATCAGCG TTACTAGCTA
3481 AGAAAAACAA GGACTTTAAT GAATGGCTAA AGATAGAATC ATTTAGAGAA ATAATAGATA
3541 CTTTAGATAA AATTAATTAC GATCTAGGAC AACGATATTG TGAAGAACTT ACGGCGCATC
3601 ACATTCCAGT GTAATTATTG AGGTCAAAGC TAGTAACTTA ATAGATGACA GGACAGCTG
```

*FIG. 2*

INFECTIOUS BURSAL DISEASE VIRUS RECOMBINATION POXVIRUS VACCINE

CROSS REFERENCE TO RELATED APPLICATIONS

This application is a division of U.S. application Ser. No. 08/303,124 filed Sep. 7, 1994, now U.S. Pat. No. 5,641,490, which in turn is a continuation of Ser. No. 07/918,311 filed Jul. 21, 1992, now abandoned, which in turn is a continuation-in-part of U.S. application Ser. No. 07/736,254 filed Jul. 26, 1991, now abandoned. Reference is also made to copending application Ser. No. 07/847,951, filed Mar. 6, 1992, now abandoned, also incorporated herein by reference.

FIELD OF THE INVENTION

The present invention relates to a modified poxvirus and to methods of making and using the same. More in particular, the invention relates to recombinant poxvirus, which virus expresses gene products of an infectious bursal disease virus (IBDV) gene, and to vaccines which provide protective immunity against IBDV infections.

Several publications are referenced in this application. Full citation to these documents is found at the end of the specification preceding the claims. These documents pertain to the field of this invention; and, each of the documents referenced in this application are hereby incorporated herein by reference.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of the vaccinia virus described in U.S. Pat. Nos. 5,110,587, 4,769,330, 4,722,848, and 4,603,112; the disclosures of each of these patents is incorporated herein by reference. Reference is also made to copending application Ser. No. 07/537,890, filed Jun. 14, 1990, also incorporated herein by reference.

First, the DNA gene sequence to be inserted into the virus, particularly an open reading frame from a non-pox source, is placed into an E. coli plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within E. coli bacteria (Clewell, 1972) and isolated (Clewell et al., 1969; Sambrook, et al., 1989).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

The technology of generating vaccinia virus recombinants has recently been extended to other members of the poxvirus family which have a more restricted host range. The avipox virus, fowlpox, has been engineered as a recombinant virus. This recombinant virus is described in PCT Publication No. WO89/03429, also incorporated herein by reference.

Fowlpox virus (FPV) has advantageously been engineered as a vector expressing antigens from poultry pathogens. The hemagglutinin protein of a virulent avian influenza virus was expressed in an FPV recombinant (Taylor et al., 1988). After inoculation of the recombinant into chickens and turkeys, an immune response was induced which was protective against either a homologous or heterologous virulent influenza virus challenge (Taylor et al., 1988). In addition, the surface glycoproteins (fusion and hemagglutinin) of a virulent strain of Newcastle Disease Virus have been expressed in an FPV vector and shown to induce a protective immune response (Taylor et al., 1990; Edbauer et al., 1990).

FPV is the prototypic virus of the Avipox genus of the Poxvirus family. The virus causes an economically important disease of poultry which has been well controlled since the 1920's by the use of live attenuated vaccines.

Replication of the avipox viruses is limited to avian species (Matthews, 1982) and there are no reports in the literature of the virus causing a productive infection in any non-avian species including man. This host restriction provides an inherent safety barrier to transmission of the virus to other species and makes use of FPV as a vaccine vector in poultry an attractive proposition.

Infectious bursal disease, also known as Gumboro's disease, manifests itself in two ways. In chickens older than three weeks, infectious bursal disease virus (IBDV) can cause impaired growth and mortality losses of up to 20% (Lukert and Hitchner, 1984). In younger birds, the disease is subclinical but is evident as microscopic lesions in the bursa of Fabricius (Winterfield et al., 1972). This results in prolonged and severe immunosuppression which causes increased susceptibility to disease and interferes with vaccination programs against other disease agents (Allan et al., 1972). Characteristics of the disease have been reviewed in Lukert and Saif (1991) and will be summarized briefly here.

The cloacal bursa appears to be the primary target organ of the virus and birds surgically bursectomized at 4 weeks have been shown to survive a lethal IBDV challenge without clinical manifestations (Kaufer and Weis, 1980). The age of bursectomy is however, critical. Schat et al., (1981) performed embryonal bursectomy and then challenged with IBDV at 2 and 6 weeks of age. Birds developed typical hemorrhagic lesions, were clinically ill and showed some mortality. The target cells are actively dividing B lymphocytes (Muller, 1986; Burkhardt and Muller, 1987). Muller (1986) demonstrated that IBDV will replicate preferentially in lymphoid cells from the bursa and poorly in lymphoid cells from other organs. It has been proposed that clinical signs of IBDV infection may result from immune complex formation (Ley et al., 1979; Skeeles et al., 1979). Muller (1986) however, demonstrated that the preferential replication in the lymphoid cells of the bursa is not related to the presence of surface immunoglobulins.

Two serotypes of IBDV, designated 1 and 2 have been demonstrated (McFerran et al., 1980; Jackwood et al., 1984; McNulty and Saif, 1988). Virulent serotypes have been shown in group 1. No disease has been associated with group 2 viruses. In addition, considerable antigenic variation has been documented within serotypes (Lukert and Saif, 1991).

The causative agent, IBDV, has been classified as a Birnavirus (Brown et al., 1986). The biochemistry and replication of IBDV has been reviewed in Kibenge et al., (1988). Birnaviruses are small non-enveloped animal viruses having two segments of double-stranded RNA. The smaller genomic segment (segment B) of IBDV encodes a single polypeptide of 90 k designated VP1. This protein is a minor internal component of the virion and is presumed to be the viral RNA polymerase (Hudson et al., 1986; Nagy et al., 1987; Spies et al., 1987). The larger genomic segment (segment A) encodes 5 polypeptides with the following designations and approximate molecular weights 52 k (VPX), 41 k (VP2), 32 k (VP3), 28 k (VP4) and 16 k (Azad et al., 1985). The identity and presence of the 16K polypeptide has not been confirmed (Kibenge et al., 1988). VP2, VP3 and VP4 arise by co-translational proteolytic cleavage of precursor polyproteins. The protein VP4 is thought to be a viral protease (Hudson et al., 1986) responsible for cleavage between VPX and VP4 (Duncan et al., 1987) and between VP4 and VP3 (Azad et al., 1987; Jagadish et al., 1988).

Protein VP2 is the most abundant protein of the viral capsid making up 51% of serotype I IBDV proteins (Dobos et al., 1979). VP2 is only found in mature viral particles and is not seen in IBDV infected cells (Becht et al., 1988). VP2 is thought to be a specific cleavage product of a VPX precursor. Peptide mapping has shown that VPX and VP2 of IBDV strain CU-1 have similar amino acid sequences (Muller and Becht, 1982; Dobos, 1979). In addition both VPX and VP2 react with the same monoclonal antibody on Western blots (Fahey et al., 1985 b; Becht et al., 1988). It has recently been demonstrated that a conformational dependent neutralizing epitope exists on VP2 (Azad et,al., 1987; Fahey et al., 1989) and a conformation independent neutralizing epitope exists on VP3 (Fahey et al., 1985 a,b). Antibodies to these epitopes were found to passively protect chickens (Fahey et al., 1985 b; Azad et al., 1987; Fahey et al. 1989). Becht et al., (1988) and Snyder et al., (1988) indicated that neutralizing monoclonal antibodies to VP2 differentiated between serotypes 1 and 2 in cross-neutralization tests. However, Becht et al., (1988) also indicated that monoclonal antibodies to VP3 recognized a group-specific antigen from both serotypes which was not associated with neutralizing activity or protection. These studies may indicate the existence of multiple epitopes at least on VP2 and perhaps on VP3.

In a recent publication, Macreadie et al., (1990) demonstrated the expression of VP2 in a yeast vector. The size of the expressed protein was consistent with that of an authentic VP2. Centrifugation and gel filtration studies indicated that the VP2 expressed in yeast was in a high molecular weight-aggregated form. Chickens inoculated with a crude extract of the yeast expressed VP2 developed an immune response as demonstrated by ELISA test and virus neutralization tests. One day old chickens were then inoculated with anti-sera from chickens previously inoculated with yeast expressed VP2. These chickens were passively protected against IBDV challenge as evidenced by lack of IBDV antigen in the bursa (Macreadie et al., 1990).

Current vaccination strategies against IBDV include both live and killed vaccines. Antibody transmitted from the hen via the yolk of the egg can protect chickens against early infections with IBDV. Therefore, use of killed vaccines in oil emulsions to stimulate high levels of maternal antibody is extensive in the field (Lukert and Saif, 1991). Studies by Lucio and Hitchner (1979) and Baxendale and Lutticken (1981) indicated that oil emulsion IBDV vaccines can stimulate adequate maternal immunity to protect chickens for 4–6 weeks. In contrast progeny from breeders vaccinated with live vaccines are protected for only 1–3 weeks after hatching (Lukert and Saif, 1991).

Determination of when maternal antibody has waned, and thus when antibody levels can be boosted by active immunization is problematical. It is therefore common practice to vaccinate all chicks against IBD with a live vaccine during the first 3 weeks of life (Winterfield et al., 1980). Inactivated vaccines are ineffective in inducing active immunity in chicks with maternal antibody. Presently available live vaccines consist of strains of intermediate virulence or highly attenuated strains, as well as some cell culture adapted variant strains. While intermediate strains can break through maternal antibody titers of approximately 1:250 (Lukert and Saif, 1991), the strains vary in virulence and can induce bursal atrophy and immunosuppression in day old and 3 week old SPF chickens (Lukert and Mazariegos, 1985).

Given the limitations of current vaccination strategies, it can be appreciated that provision of an IBDV recombinant poxvirus, and of vaccines which provide protective immunity against IBDV infections, would be a highly desirable advance over the current state of technology.

OBJECTS OF THE INVENTION

It is therefore an object of this invention to provide recombinant poxviruses, which viruses express gene products of IBDV, and to provide a method of making such recombinant poxviruses.

It is an additional object of this invention to provide for the cloning and expression of IBDV coding sequences, particularly sequences coding for IBDV structural proteins, in a poxvirus vector, particularly fowlpox virus.

It is another object of this invention to provide a vaccine which is capable of eliciting IBDV antibodies and protective immunity against IBDV infection.

These and other objects and advantages of the present invention will become more readily apparent after consideration of the following.

STATEMENT OF THE INVENTION

In one aspect, the present invention relates to a recombinant poxvirus containing therein a DNA sequence from IBDV in a nonessential region of the poxvirus genome. The poxvirus is advantageously an avipox virus, such as fowlpox virus.

According to the present invention, the recombinant poxvirus expresses gene products of the foreign IBDV gene. In particular, the foreign DNA codes for IBDV structural proteins. The IBDV gene may be co-expressed with other foreign genes in the host by the recombinant poxvirus.

In another aspect, the present invention relates to a vaccine for inducing an immunological response in a host animal inoculated with the vaccine, said vaccine including a carrier and a recombinant poxvirus containing, in a nonessential region thereof, DNA from IBDV. Advantageously, the DNA codes for and expresses IBDV structural proteins. The IBDV gene may be co-expressed with other foreign genes in the host. The poxvirus used in the vaccine according to the present invention is advantageously an avipox virus, such as fowlpox virus, referred to hereafter as TROVAC.

BRIEF DESCRIPTION OF THE DRAWINGS

A better understanding of the present invention will be had by referring to the accompanying drawings, in which:

FIG. 1 (SEQ ID NO:7) shows the nucleotide sequence of a 3661 base pair fragment of TROVAC DNA containing the F8 open reading frame; and FIG. 2 (SEQ ID NO:12) shows the nucleotide sequence of a 3659 base pair fragment of TROVAC DNA containing the F8 open reading frame.

DETAILED DESCRIPTION OF THE INVENTION

The invention is directed to recombinant poxviruses containing therein a DNA sequence from IBDV in a nonessential region of the poxvirus genome. The recombinant poxviruses express gene products of the foreign IBDV gene. In particular, IBDV genes encoding IBDV structural proteins were isolated, characterized and inserted into TROVAC (FPV) recombinants.

Cell Lines and Virus Strains. The strain of FPV designated FP-1 has been previously described (Taylor et al., 1988). It is an attenuated vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast (CEF) cells. This virus was obtained in September 1980 by Rhone Merieux, Lyon, France and a master viral seed established. Subsequently, the virus was subjected to four successive plaque purifications. One plaque isolate was further amplified in primary CEF cells, and a stock virus, designated as TROVAC, established. TROVAC was deposited on Feb. 6, 1997 under the terms of the Budapest Treaty with the American Type Culture Collection (ATCC), 12301 Parklawn Drive, Rockville, Md., 20852, USA, ATCC accession number VR-2553.

cDNA clones from IBDV strain Faragher (Type I) were obtained from Rhone Merieux, Lyon, France.

EXAMPLE 1

Construction of Insertion Vector for IBDV-VP2

Plasmid pIBDVA contains a 3.1 Kb KpnI to XbaI fragment derived from CDNA clones of IBDV strain Faragher. This fragment was inserted into vector pBluescript II SK+ (Stratagene, La Jolla, Calif.). The insert corresponds to the segment A of the IBDV genome which encodes the 108 kDa precursor polyprotein. The polyprotein is subsequently processed to form VP2, VP3 and VP4.

In order to isolate the coding sequence for VP2 from pIBDVA, VP3 and VP4 coding sequences were deleted from pIBDVA and a termination codon added to the 3' end of the VP2 coding sequence. This was accomplished by digestion of pIBDVA with ScaI and KpnI and insertion of the annealed and kinased oligonucleotides CE279 (SEQ ID NO:1) and CE280 (SEQ ID NO:2) to form pCEN112.

CE279

ACTTCATGGAGGTGGCCGACCT-
CAACTCTCCCCTGAAGATTGCAGGAG-
CATTTGG CTTCAAAGACATAATCCGGGC-
TATAAGGAGGTGAGTCGACGGTAC

CE280

CGTCGACTCACCTCCTTATAGCCCGGAT-
TATGTCTTTGAAGCCAAATGCTCCTGC AATCT-
TCAGGGGAGAGTTGAGGTCGGCCACCTC-
CATGAAGT

The vaccinia virus H6 promoter previously described in Taylor et al., (1988); Guo et al., (1989), Perkus et al., (1989), was inserted into pCEN112 by digesting pCEN112 with NotI, and blunt-ending with the Klenow fragment of DNA polymerase, in the presence of 10 mM dNTPs. A HindIII to EcoRV fragment which contains the H6 promoter was blunt-ended with the Klenow fragment of DNA polymerase and inserted into the linearized pCEN112 to generate pCEN117.

In order to couple the promoter sequence with the initiating ATG of IBDV VP2 coding sequence, the annealed and kinased oligonucleotides CE277 (SEQ ID NO:3) and CE278 (SEQ ID NO:4) were inserted into pCEN117 that had been digested with NruI and RsrII. The resulting plasmid was designated pCEN120.

CE277

CGATATCATGACAAACCTGCAAGAT-
CAAACCCAACAGATTGTTCCGTTCATACGG
AGCCTTCTGATGCCAACAACCG

CE278

GTCCGGTTGTTGGCATCAGAAGGCTCCG-
TATGAACGGAACAATCTGTTGGGTTTG ATCT-
TGCAGGTTTGTCATGATATCG

A SmaI to SalI fragment from pCEN120, containing IBDV-VP2 linked to the vaccinia virus H6 promoter was cloned into the HpaI and SalI sites of the FPV insertion vector pCEN100 (described below) to generate pCEN137. Plasmid pCEN137 was used in an in vitro recombination test to generate recombinant vFP115.

EXAMPLE 2

Construction of Insertion Vector for IBDV VP2, VP3, VP4

Non-coding sequence was removed from the 3' end of the IBDV polyprotein sequence by partially digesting pIBDVA with PpuMI, completely digesting with KDnI, and re-inserting the annealed and kinased oligonucleotides CE275 (SEQ ID NO:5) and CE276 (SEQ ID NO:6) into pIBDVA to generate pCEN111.

CE275: GACCTTGAGTGAGTCGACGGTAC

CE276: CGTCGACTCACTCAAG

A perfect 5' end to the polyprotein sequence was obtained in the following manner. A KpnI-BstEII fragment containing the majority of the polyprotein sequence with a perfect 3' end was excised from pCEN111 and ligated into the KpnI and BstEII sites of pCEN120. This substitution replaces the 3' end of the VP2 coding sequence and generates a perfect 5' end for the polyprotein with linkage to the vaccinia virus H6 promoter. The resulting plasmid was designated pCEN125. The final insertion plasmid was constructed by partial digestion of pCEN125 with SmaI and complete digestion with SalI. The resulting fragment was cloned into the HpaI and SalI sites of pCEN100 (described below) to form pCEN138. Plasmid pCEN138 was used in an in vitro recombination test to generate recombinant vFP116.

EXAMPLE 3

Construction of Fowlpox Insertion Plasmid at F8 Locus

Plasmid pRW731.15 contains a 10 Kbp PvuII—PvuII fragment cloned from TROVAC genomic DNA. The nucleotide sequence was determined on both strands for a 3661 bp PvuII-EcoRV fragment. This sequence is shown in FIG. 1 (SEQ ID NO:7). The limits of an open reading frame designated in this laboratory as F8 were determined within this sequence.

Subsequently, the nucleotide sequence of FIG. 1 was further analyzed and was determined on both strands to be a 3659 bp PvuII-EcoRV fragment. This sequence is shown in FIG. 2 (SEQ ID NO:12). The limits of the open reading frame designated in this laboratory as F8 were determined within this sequence; and, the subsequent determination of the sequence, as shown in FIG. 2, does not affect the reproducibility of this or any other construction involving the fowlpox F8 locus determined by this laboratory, especially because the deletions and insertions into the F8 ORF can be performed by the skilled artisan following the teachings from this laboratory, such as the following description, without recourse to the sequence of the F8 ORF or the PvuII-EcoRV fragment within which it is contained. Based on sequence information contained in FIG. 2, the open reading frame is initiated at position 495 and terminates at position 1887. A deletion was engineered from what was ultimately determined to be position 779 to position 1926, as described below.

Plasmid pRW761 is a sub-clone of pRW731.15 containing a 2430 bp EcoRV—EcoRV fragment. Plasmid pRW761 was completely digested with XbaI and partially digested with SspI. A 3700 bp XbaI-SspI band was isolated and ligated with the annealed double-stranded oligonucleotides JCA017 (SEQ ID NO:8) and JCA018 (SEQ ID NO:9). JCA017 5' CTAGACACTTTATGTTTTTTAATATCCG-GTCTTAAAAGCTTCCCGGGGGA TCCTTATACGCG-GAATAAT 3'

JCA018 5' ATTATTCCCCGTATAAGGATCCCCCGG-GAAGCTTTTAAGACCGGATATTA AAAAACAT-AAAGTGT 3'

The plasmid resulting from this ligation was designated pJCA002.

Additional cloning sites were incorporated into pJCA002 by inserting the annealed and kinased oligonucleotides CE205 (SEQ ID NO:10) and CE206 (SEQ ID NO:11) into the BamHI and HindIII sites of pJCA002 to form pCE72.

CE205: GATCAGAAAAACTAGCTAGCTAGTACG-TAGTTAACGTCGACCTGCAGAAG CTTCTAGCTAGCTAGTTTTTAT

CE206: AGCTATAAAAACTAGCTAGCTAGAAGCT-TCTGCAGGTCGACGTTAACTAC GTAC-TAGCTAGCTAGTTTTTCT

In order to increase the length of the FPV flanking arms in the insertion plasmid, plasmid pJCA021 was constructed. Plasmid pJCA021 was obtained by inserting a 4900bp PvuII-HindII fragment from pRW731.15 (described above) into the SmaI and HindII sites of pBluescript SK+ (Stratagene, La Jolla, Calif.). A BglII to EcoRI fragment from pCEN72 was then ligated into the BglII and EcoRI sites of pJCA021 to generate pCEN100.

EXAMPLE 4

Development of TROCAC-IBDV Recombinants

Plasmids pCEN137 and pCEN138 were transfected into TROVAC infected primary CEF cells by using the calcium phosphate precipitation method previously described (Panicali and Paoletti, 1982; Piccini et al., 1987). Positive plaques were selected on the basis of hybridization to specific IBDV radiolabeled probes and subjected to five sequential rounds of plaque purification until a pure population was achieved. One representative plaque from each IVR was then amplified and the resulting TROVAC recombinants were designated vFP115 (IBDV-VP2) and vFP116 (IBDV-VP2, VP3, VP4).

Immunofluorescence. In order to determine where the IBDV proteins were localized in recombinant infected CEF cells, immunofluorescence analysis was performed. Indirect immunofluorescence was performed was performed as described in Taylor et al., (1990) using a neutralizing monoclonal antibody preparation specific for VP2 and designated AC6 and a VP3 specific monoclonal antibody designated NA3 obtained from Rhone Merieux. In addition, a polyclonal chicken anti-IBDV serum was obtained from Spafas Inc., Storrs, Conn.

The results indicated that IBDV specific immunofluorescence could be detected in the cytoplasm of cells infected with either vFP115 or vFP116. No fluorescence was detected in parental TROVAC infected CEF cells. No surface fluorescence was detected in cells infected with either recombinant virus. Equivalent results were obtained using both the neutralizing monoclonal antibody preparation and the polyclonal immune serum. The result was not unexpected since the analysis of the sequence of the IBDV genes does not indicate the presence of characteristic signal and anchor sequences which would direct insertion of the proteins in the infected cell membrane.

Immunoprecipitation. Immunoprecipitation reactions were performed as described in Taylor et al., (1990) using the monoclonal antibody preparations and the polyclonal anti-IBDV immune serum from chickens as described above.

Immunoprecipitation analysis of CEF cells infected with recombinant vFP115 indicated the expression of a protein of approximately 38–40 Kd recognized by both polyclonal immune sera and the neutralizing monoclonal antibody. This size is appropriate for expression of the structural protein, VP2 (Azad et al., 1985). Immunoprecipitation analysis of lysates of cells infected with recombinant vFP116 encoding the IBDV polyprotein, with the same serological reagents, also demonstrated expression of a single protein species of approximately 43 kd. This protein is recognized by both polyclonal immune serum and the neutralizing monoclonal antibody preparation. Both the size of the protein and its recognition by the monoclonal antibody indicate that the identity of this protein may be VPX, the precursor to VP2. Although no other proteins are immunoprecipitated by the polyclonal immune serum, presence of the cleaved VPX indicates that VP4, the cleavage protein is probably expressed. Since VP4 is a very minor component of the virion, it is not unusual that the immune serum should not contain antibodies to this protein. Use of the VP3 specific monoclonal antibody indicated the expression of a protein of 32 kd in cells infected with vFP116.

EXAMPLE 5

Immunization of Chickens and Subsequent Challenge

Groups of 20, 5 day old susceptible SPF chickens were inoculated by subcutaneous injection in the nape of the neck with 0.2 ml of recombinants vFP115 or vFP116. This corresponded to a dose of approximately $4.0 \log_{10} TCID_{50}$. A group of 19 birds were left as uninoculated controls. At fourteen days post vaccination, chickens were bled and serum neutralizing titers in the sera were determined. Birds were challenged at 14 days by intra-ocular inoculation of 0.03 ml of the virulent heterologous serotype I IBDV challenge strain (designated STC) supplied by the USDA National Veterinary Services Laboratory. Five days after challenge, each chicken was necropsied and the bursa examined for gross lesions and the appearance of atrophy. The results are shown in Table 1.

The results indicate that inoculation of one dose of vFP115 expressing the VP2 structural protein leads to the induction of serum neutralizing antibody and 75% protection of challenged birds. Inoculation of vFP116 leads to the induction of a poor neutralizing antibody response but 50% of challenged birds are protected.

TABLE 1

Protective Efficacy of TROVAC-IBDV Recombinants in Chickens

| Recombinant | #Protected/Challenged[b] | % Protection | SN Titer[a] |
|---|---|---|---|
| vFP115 | 15/20 | 75 | 131 |
| vFP116 | 10/19 | 53 | 6 |
| Controls | 0/19 | 0 | 0 |

[a]Serum neutralization titer
[b]Birds are considered protected in the absence of bursal atrophy and lesions.

EXAMPLE 6

IBDV Recombinant Poxvirus Vaccines

Recombinant poxviruses containing, in a nonessential region thereof, DNA from IBDV provide advantages as vaccines for inducing an immunological response in a host animal. Infectious bursal disease virus is very stable and persists in the environment for long periods. For economic reasons, poultry houses are rarely cleaned between broods and thus chickens are exposed to the virus early in life. Since elimination of virus by hygienic means is not possible, vaccination strategies need to be formed. Active immunization of chickens is difficult in the presence of maternal antibody. In addition, since maternal antibody levels are variable and the rate of loss of antibody unpredictable, timing of vaccination is a problem. A successful vaccine will need to be able to boost immunity in the presence of maternal antibody and should also contain cross-reactive antigens from a number of different serotypes. In addition, an effective vaccine should not induce signs of disease in vaccinated birds.

TROVAC-IBDV recombinant vFP115 expressed the major structural protein VP2 which has been shown to contain at least one highly immunogenic region. The protein expressed by the TROVAC recombinant is recognizable by IBDV immune serum. Inoculation of this recombinant into susceptible birds resulted in 75% protection from bursal damage. Recombinant vFP116 contains the coding sequence for the polyprotein VP2, VP3, VP4. A protein probably corresponding to VPX, the VP2 precursor, was expressed which is also recognized by IBDV immune sera. Inoculation of this recombinant into susceptible birds lead to the development of low neutralizing antibody levels, but induced 53% protection from bursal damage.

The results indicate the potential of TROVAC-IBDV recombinants for vaccination against IBDV in the poultry industry. The restricted host range of FPV provides an inherent safety barrier to transmission of recombinant to non-vaccinated species. Use of antigenic regions of IBDV rather than whole virus eliminates the need to introduce live virus to the environment and may lessen the immunological pressure on the virus which leads to the emergence of variant strains. The large size of the FPV genome allows incorporation of multiple antigenic sequences and should allow for vaccination against a variety of strains.

EXAMPLE 7

Further Immunogenicity and Efficacy Studies with vFP115

Effect of dose of inoculation on protective efficacy induced by vFP115. Groups of day old SPF chickens were inoculated with vFP115 by the subcutaneous route in the nape of the neck. The virus was administered in doses of 4.9, 5.5 or 6.2 $\log_{10} EID_{50}$ per bird. At 21 days post-vaccination, ten vaccinates and ten naive birds were bled and the sera analyzed for the presence of IBDV specific serum neutralizing (SN) antibody. At 28 days, birds were challenged by administration by the ocular route of 1.3 $\log_{10} EID_{50}$ of the heterologous Standard Challenge Strain of IBDV. At 5 days post-challenge, 5 birds from each group were necropsied and bursae examined for gross lesions. At 11 days post-challenge, the remaining birds were killed and bursa to body weight ratios determined. The results of analysis are shown in Table 2. The results indicate that increasing the inoculation dose has led to the induction of slightly higher levels of SN antibody, but that the protective efficacy is not enhanced. Birds were considered protected when the bursa to body weight ratio after challenge was greater than one standard deviation of the mean bursa to body weight ratio of infected control birds. Using this criteria, and considering bursa to body weight ratios of individual birds, protection ratios of 65%, 74% and 64% were obtained for VFP115 dosages of 4.9, 5.5 and 6.2 $\log_{10} EID_{50}$ respectively.

TABLE 2

Dose Response Study of Inoculation of vFP115 in Day Old Chickens

| Dose | SN GMT[a] | Bursal Lesions[b] Positive/Total | Bursa/Body Weight Ratio[c] |
|---|---|---|---|
| 4.9 | 13 | 1/5 | 3.5 |
| 5.5 | 35 | 2/5 | 3.2 |
| 6.2 | 102 | 1/5 | 3.2 |
| Control | 0 | 5/5 | 1.6 |

[a]Geometric Mean Titer of sera of 10 birds
[b]Bursa of 5 birds examined for gross lesions
[c]Ratio expressed as a mean of 23 birds Effect of Age of Bird on Protective Efficacy of vFP115. Groups of 30 one-, four-, seven- and fourteen day old SPF birds were inoculated by the subcutaneous route with 4.0 $\log_{10}$ EID$_{50}$ of vFP115. At 21 days post-vaccination, 10 vaccinates and 5 naive controls of each group were bled and sera analyzed for the presence of SN antibody. At 28 days post-vaccination, all vaccinates and naive controls were challenged by the ocular route with 1.3 $\log_{10}$ EID$_{50}$ of the heterologous STC virus strain. Four days post-challenge, birds were sacrificed and bursa examined for evidence of bursal damage. The results of analysis are shown in Table 3. The results indicate that while IBD specific SN titers and protection after challenge are obtained at one day of age, when vaccination is delayed past 4 days of age higher SN titers are obtained and the level of protection is increased.

TABLE 3

Effect of Age of Bird on Protective Efficacy of VFP115

| Age Group | Treatment | GMT | Protection Ratio | % Protection |
|---|---|---|---|---|
| 1 day | Vaccinates | 126 | 23/30 | 77 |
|  | Controls |  | 0/10 | 0 |
| 4 days | Vaccinates | 666 | 25/30 | 83 |
|  | Controls |  | 0/10 | 0 |
| 7 days | Vaccinates | 1946 | 29/30 | 97 |
|  | Controls |  | 1/10 | 0 |
| 14 days | Vaccinates | 1408 | 30/30 | 100 |
|  | Controls |  | 0/10 | 0 |

Effect of route of inoculation on induction of a protective immune response by vFP115. Groups of twenty 14 day old SPF birds were inoculated by (a) the intramuscular route in the leg, (b) ocular route or (c) oral route with 4.0 $\log_{10}$TCID$_{50}$ of vFP115. At 14 and 28 days post-inoculation sera were collected and analyzed for the presence of IBDV specific SN antibody. At both 14 and 28 days post-vaccination, groups of birds were challenged by ocular inoculation of 2.5 $\log_{10}$EID$_{50}$ of the homologous Faragher strain of IBDV. Deaths were recorded and at 4 days post-challenge all birds were sacrificed and Bursa examined for the presence of macroscopic lesions. Significant neutralizing antibody responses were found only after inoculation of vFP115 by the intramuscular route with SN titers of approximately 2.0 $\log_{10}$ at 14 and 28 days post-inoculation. By ocular and oral routes, low SN titers were achieved in 30 and 10% of chickens, respectively. The results of challenge are shown in Table 4. All birds inoculated with vFP115 by the intramuscular route were fully protected from challenge which was pathogenic in all control non-vaccinated birds at 14 and 28 days post-inoculation. No protection was observed following the oral route of inoculation. Partial protection was seen by the ocular route.

TABLE 4

Effect of Route of Inoculation on Protective Efficacy Induced By vFP115

| Route of Inoculation | % Protection from challenge at | |
|---|---|---|
|  | 14 days post-vacc | 28 days post-vacc |
| Intramuscular | 100 | 100 |
| Ocular | 50 | 10 |
| Oral | 0 | 0 |

EXAMPLE 8

Development of a TROVAC Recombinant Expressing The VP3 Structural Protein

Example 2 describes the development of a TROVAC based recombinant vFP116 expressing the VP2, VP4, VP3 polyprotein. Efficacy studies described in Example 5 indicate that this recombinant induces lower levels of protection than vFP115 expressing the VP2 protein after inoculation into susceptible chickens. In vitro studies showed that the VP2 protein expressed in the vFP116 construct is slightly larger than that expressed in the vFP115 construct and that expression of the VP3 protein is not detectable by a polyclonal serum. Immunofluorescence and immunoprecipitation analysis with a VP3 specific monoclonal antibody, however, indicated that the VP3 protein is expressed in vFP116. In order to evaluate the role of the VP3 protein in eliciting cross-protective immunity, a single recombinant was developed expressing the VP3 protein from the Faragher strain of IBDV.

Construction of a Fowlpox Insertion Plasmid at the F16 Locus. The plasmid pFP23K (described by Tartaglia et al., 1990) contains a 10.5 kb HindIII fragment from the fowlpox (FP) genome. A 7.3 kb NaeI\NdeI FP fragment was isolated from pFP23K and ligated to a similarly cut pUC9 vector to generate pRW866. A unique FspI site within this FP fragment lies between two ORFs (intergenic region) and is the F16 insertion locus.

In order to create a multiple cloning site (MCS) cassette for the F16 locus, two PCR fragments were amplified from pFP23K using primers RW264 (SEQ ID NO:13) plus RW265 (SEQ ID NO:14) and RW266 (SEQ ID NO:15) plus RW267 (SEQ ID NO:16). The resulting fragments were mixed together and amplified with primers RW266 and RW267 which resulted in a single, fused fragment. This fragment was digested with EcoRI and NdeI and ligated into similarly cut pRW715 (derived from pUC9 by digesting with PvuII and ligating an EcoRI linker between the two PvuII sites), to yield pRW864. The MCS cassette consists of a polycloning region (SmaI-BamHI-HindIII sites) flanked on either side by translational stop codons in all six reading frames and a NotI site. A vaccinia early transcriptional stop signal is located on the HindIII end.

RW264: AATTAACCCGGGATCCAAGCT-TCTAGCTAGCTAATTTTT ATAGCGGCCGC-TATAATCGTTAACTTATTAG

RW265: CTAGCTAGAAGCTTGGATCCCGGGT-TAATTAATTAATAAAAA GCGGCCGCGTTAAAG-TAGAAAAATG

RW266: GTTACATATGTACAGAATCTGATCATAG

RW267: GCTAGAATTCTCTTAGTTTTTATAGTTG

The following describes a series of plasmid constructs which ultimately leads to the MCS cassette from pRW864 being inserted into the FspI site of pRW866 to generate the F16 insertion plasmid (pRW873). A cassette containing the E. coli lacZ gene coupled to the vaccinia 11K promoter was excised from pAM1BG as a BamHI/PstI fragment. Plasmid PAMIBG contains the lacZ BamHI fragment from pMC1871 (Casadaban et al., 1983) inserted in the previously described BamHI site 3' of the 11K vaccinia virus promoter (Paoletti et al., 1984). The ends were repaired using Klenow polymerase and the cassette ligated into pRW864 cut with SmaI to yield pRW867A. The lacZ gene cassette was excised from pRW867A using NotI and the ends repaired with Klenow polymerase. This fragment was then ligated into the unique FspI site in the FP sequences of pRW866 resulting in pRW868. The lacZ gene from pRW868 was excised using NotI and replaced with the MCS cassette derived as a NotI fragment from pRW864 resulting in pRW873, the F16 insertion plasmid.

Development of an FP recombinant expressing VP3. The complete IBDV VP3 ORF was excised from pCEN111 (described in Example 3) as a 1262 bp BamHI and Asp718 fragment and ligated into a similarly cut pSD554VC (a vaccinia donor plasmid containing the H6 promoter) to yield pFT1. A 112 bp PCR fragment was amplified from pCEN111 using oligonucleotides JP003 (SEQ ID NO:17) and JP004 (SEQ ID NO:18), digested with NruI/ScaI, and gel purified. This fragment was ligated into pFT1 digested completely with NruI and partially with ScaI to yield pIBDV-VP3II. This plasmid contains the vaccinia H6 promoter coupled to the VP3 ORF.

A PCR fragment was amplified from pRW823 which contains vaccinia virus H6 promoter sequences using oligonucleotides RG662 (SEQ ID NO:19) and RG663 (SEQ ID NO:20). This fragment was digested with HindIII/SmaI and ligated into the F16 insertion plasmid (pRW873) cut with the same enzymes resulting in pF16VQH6. A cassette containing part of the H6 promoter fused to the VP3 ORF was excised from pIBDV-VP3II with NruI/Asn718, the ends repaired with Klenow polymerase, and the purified fragment ligated into pF16VQH6 cut with NruI/SmaI to generate the donor plasmid pF16VP3F.

JP003 5'-AAGGTAGTACTGGCGTCC-3'

JP004 5'-TTATCGCGATATCCGTTAAGTTTGTA-TCGTAATATGTTCCCTCACAATCCACGA-3'

RG662 5'-TAAAAGCTTTTAATTAATTAGTCATC-3'

RG663 5'-TAACCCGGGCGATACAAACTTAACGG-3'

Plasmid pF16VP3F was used in in vitro recombination with TROVAC as the rescuing virus to derive recombinant vFP186. Immunoprecipitation analysis using a VP3 specific monoclonal antibody has confirmed the expression of a protein of approximately 32 kd in CEF cells infected with the recombinant.

EXAMPLE 9

Development of TROVAC Based Recombinants with Altered Modes of Expression of the VP2 Protein It has been postulated that a protein displayed on the infected cell surface may lead to a more efficient induction of neutralizing antibody than if the protein is secreted or expressed internally. Previous studies have indicated that expression of a foreign antigen on the infected cell surface by a recombinant vaccinia virus, can be achieved by recombinant DNA techniques by adding appropriate signal and anchor sequences (Langford et al., 1986; Vijaya et al., 1988). The VP2 protein in IBDV infected cells is not a membrane bound glycoprotein and possesses neither an endogenous signal nor anchor sequences. A strategy was devised to add the appropriate signal and anchor sequences from the Newcastle Disease Virus fusion protein. The fusion protein is an integral membrane bound glycoprotein. This strategy is described below.

The IBDV VP2 ORF plus translational stop codon was excised from pCEN112 (described in Example 1) as an XbaI/SalI fragment and the ends repaired using Klenow polymerase. This cassette was ligated into the HindII site of pUC18 to generate pCE147. The vaccinia H6 promoter coupled to the NDV fusion gene signal sequence was obtained by isolating a HindIII/PstI fragment from pcE64 (for complete NDV Fusion sequences see Taylor et al., 1990). This fragment contains the H6 promoter fused to the first 25 codons from the N-terminus of the NDV fusion ORF. This fragment was ligated into pCE147 cut with HindIII/PstI to yield pCEN150.

In order to couple the last codon from the NDV fusion signal sequence with the first codon from the VP2 ORF, a PCR fragment was amplified from pCEN150 using oligonucleotides CE329 (SEQ ID NO:21) and CE330 (SEQ ID NO:22) as primers. The fragment was digested with KpnI/RsrII and ligated into pCEN150 cut with the same enzymes to generate pCEN156. The H6 promoted-NDV fusion signal sequence-VP2 ORF cassette was excised from pCEN156 with HindIII/EcoRI, the ends repaired using Klenow polymerase, and the cassette ligated into pCEN100 (the F8 insertion plasmid) cut with HpaI to generate the donor plasmid pIBDV-VP2-SS.

CE329 5'-GATCCCGGTACCTCTAATGCTGATCAT-CCGAACCGCGCTGACACTGAGCTGTACAAAC-CTGCAAGATCAAAC-3'

CE330 5'-GGACGCCGGTCCGGTTGTTGGCATC-3'

To add the NDV fusion transmembrane sequences to the above plasmid, a 240 bp PCR fragment was amplified from pIBDV-VP2-SS using primers RG583 (SEQ ID NO:23) and RG590 (SEQ ID NO:24). This coagment contains 49 codons plus stop codon from the C-terminus of the NDV fusion ORF (see Taylor et al., 1990). The purified fragment was digested with ScaI/BamHI and ligated into pIBDV-VP2-SS cut completely with BamHI and partially with ScaI to generate the donor plasmid pIBDV-VP2-SSA.

RG583 5'-GTGAGTACTTCATGGAGGTGGCC-GACCTCAACTCTCCCCTGAAGATTGCAGGAG-CATTTGGCTTCAAAGACATAATCCGGGCTATA-AGGA-GGATCGTTTTAACTGTCATATC-3'

RG590 5'-TTAGGATCCTCATATTTTTGTAGTG-GCTCTC-3'

In vitro recombination using plasmid pIBDV-VP2-SS and TROVAC as the rescuing virus generated recombinant vFP147. Expression analysis of this recombinant with both polyclonal immune serum and a VP2 specific monoclonal antibody indicated that the VP2 protein is expressed internally, and in addition is secreted into the tissue culture fluid. This result is in keeping with the addition of a signal sequence to the coding sequence of the VP2 protein. In vitro recombination using plasmid pIBDV-VP2-SSA and TROVAC as the rescuing virus generated recombinant vFP151. Expression analysis using both polyclonal immune serum and the VP2 specific monoclonal antibody indicated that the VP2 protein is expressed at the infected cell surface as expected following the addition of an anchor sequence. The fact that the VP2 protein is still recognized by the monoclonal antibody in this form of presentation indicates that conformation of this particular epitope has not been altered by the manipulations.

Efficacy studies were performed by inoculating day-old SPF chickens with 4.0 $\log_{10}$ TCID$_{50}$ of each recombinant. At 28 days birds were challenged by ocular inoculation of the heterologous STC challenge strain. In contrast to previous results obtained with the unmodified VP2 expressed in vFP115, no protection was obtained after vaccination with either vFP147 or vFP151. Further in vitro studies using tunicamycin, an inhibitor of N-linked glycosylation, have indicated that the modified VP2 proteins expressed by both vFP147 and vFP151 are glycosylated whereas the unmodified VP2 expressed in vFP115 is not. It is postulated that the addition of sugar moieties to the VP2 protein may alter conformation of the protein in areas apart from the neutralizing epitope. Alternatively, the addition of the signal and anchor sequences as constructed here, may alter conformation of the protein. In either case it appears that the antibody induced by the modified constructions is not able to neutralize the heterologous challenge virus (STC). However, vFP147 and vFP151 and products therefrom are nonetheless useful. The modified VP2 expressed by these recombinants can be used as precursors to generate the VP2 protein; for example, by removal of the additional sugar moieties or to isolate secreted VP2 protein from tissue culture supernatant for further purification.

EXAMPLE 10

Development of Poxvirus Recombinants Expressing the VP2 Protein from Heterologous Strains of IBDV IBDV strains show considerable variation in their ability to cross-neutralize. Sequence analysis of different strains has shown that one critical region involved in virus neutralization resides within a conformational epitope located on VP2. Sequence information for VP2 is available for the Faragher (Bayliss et al., 1990) and STC (Kibenge et al., 1990) strains and it has been determined that five amino acid differences between the two strains occur within the conformational epitope. A strategy was therefore devised to alter the coding sequence of the Faragher strain conformational epitope to conform with the sequence of the STC strain. This procedure is described below.

Mutagenesis of VP2 Faraaher to VP2 STC. In order to change the VP2 Faragher sequence in pCEN120 (described in Example 1) to the VP2 STC sequence, five codons were changed in the VP2 ORF using PCR site directed mutagenesis (see Kibenge et al., 1990 for STC sequence). Oligonucleotide primers RG677 (SEQ ID NO:25) plus RG678 (SEQ ID NO:26) and RG685 (SEQ ID NO:27) plus RG686P (SEQ ID NO:28) were used to amplify a 530 bp and a 270 bp fragment respectively from pCEN100 (described in Example 3). The gel purified 270 bp fragment was further amplified using oligonucleotides RG702 (SEQ ID NO:29) and RG704 (SEQ ID NO:30). The 530 bp fragment was digested with SacI and partially digested with PstI. The 270 bp fragment was digested with SacI and NcoI. These purified PCR amplified fragments, which contain the five STC codon changes, were ligated into pCEN120 cut with PstI and NcoI. The resulting plasmid, pVP2-STC was confirmed by DNA sequencing analysis.

RG677 5'-TACACACTGCAGAGCAATGGGAACCT-CAAGTTCGATCAGATG-3'

RG678 5'-GAAACACGAGCTCTCCCCCAACGC-TGAGGCTTGTGATAG-3'

RG685 5'-GGAAGAGCTCGTGTTTCAAACAAG-CGTCCAAGGCCTTGTACTGGGCGCCACCATC-TACTTTATAGGCTTTGATGGGACTACGGTAATC-ACCAGAGCTGTAGCCGCAGATAATGGGCTGA-CGGCCGGCACCGACAATCTTATGCCATTCAAT-CTTG-3'

RG686 5'-CCACCATGGATCGTCACTGCTAGGCT-CCCACTTGCCGACCATGACATCTGATCCCCTG-CCTGACCACCACTTTTGGAGGTCACTACCTC-CAGTTTGATGGATGTGATTGGCTGGGTTATCT-CATTGGTTGGAATGACAAGATTGAATGGCAT-AAG-3'

RG702 5'-GGGAGAGCTCGTGTTTCAAACAAGCG-3'

RG704 5'-CCACCATGGATCGTCACTGC-3'

Construction of the new F8 insertion plasmid. In order to remove all of F8 coding sequences from the original F8 insertion plasmid (pCEN100), a new F8 insertion plasmid was constructed. pJCA021 contains a 4900 bp PvuII/HindII fragment from TROVAC which includes the F8 gene and flanking sequences. A 4.2 kb NciI/PpuMI fragment was isolated from this plasmid and the ends repaired with Klenow polymerase. This fragment was ligated into pBluescript SK+ cut with XbaI/Asp718 and repaired with Klenow polymerase to yield pIY.

The strategy to delete the F8 ORF from pIY and replace it with a multiple cloning site (MCS) used PCR amplification of two fragments from pJCA021 with oligonucleotide primers containing the multiple cloning sequences. A 335 bp fragment was amplified from pJCA021 using oligonucleotides RG714 (SEQ ID NO:31) and RG715 (SEQ ID NO:32) and digested with HindIII and EcoRI. Similarly, a 465 bp fragment was amplified from pJCA021 using oligonucleotides RG716 (SEQ ID NO:33) and RG717 (SEQ ID NO:34) and digested with HindIII and BalII. The two PCR fragments were ligated into pIY cut with EcoRI and BglII in a three fragment ligation resulting in pFS. This plasmid is the new F8 insertion plasmid which contains a MCS consisting of SmaI, NruI, HindIII, BamHI and XhoI sites flanked by vaccinia early transcriptional stop signals and translational stops in all six frames. The length of the left arm is about 1430 bp and the length of the right arm is about 1380 bp. The F8 gene ORF which initiates at nucleotide position 495 and terminates at nucleotide position 1887 (FIG. 2) is completely deleted.

RG714 5'-AACATATTTCCGAACAG-3'

RG715 5'-TCCAAGCTTTCGCGACCCGGGTTT-TTATTAGCTAATTAGCAATATAGATTCAATATG-3'

RG716 5'-ATCAAGCTTGGATCCCTCGAGTTT-TTATTGACTAGTTAATCATAAGATAAATAATAT-ACAGC-3'

RG717 5'-GATATAGAAGATACCAG-3'

Construction of donor plasmids and recombinants expressing VP2 STC. A cassette containing the H6 promoted VP2 (STC) ORF was excised as a 1.5 kb SmaI-Asp718 fragment from pVP2-STC. The ends were repaired using Klenow polymerase and ligated into pF8 cut with SmaI to generate the pF8-STC donor plasmid.

Plasmid pFβ-STC was used in in vitro recombination with TROVAC as the rescuing virus to generate recombinant vFP209. Expression analysis of the recombinants using a polyclonal IBDV serum from chicken indicated that the VP2 protein is expressed internally in CEF cells infected by the recombinant.

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
ACTTCATGGA GGTGGCCGAC CTCAACTCTC CCCTGAAGAT TGCAGGAGCA TTTGGCTTCA      60
AAGACATAAT CCGGGCTATA AGGAGGTGAG TCGACGGTAC                          100
```

( 2 ) INFORMATION FOR SEQ ID NO:2:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
CGTCGACTCA CCTCCTTATA GCCCGGATTA TGTCTTTGAA GCCAAATGCT CCTGCAATCT      60
TCAGGGAGA GTTGAGGTCG GCCACCTCCA TGAAGT                                96
```

( 2 ) INFORMATION FOR SEQ ID NO:3:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
CGATATCATG ACAAACCTGC AAGATCAAAC CAACAGATT GTTCCGTTCA TACGGAGCCT      60
TCTGATGCCA ACAACCG                                                    77
```

( 2 ) INFORMATION FOR SEQ ID NO:4:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
GTCCGGTTGT TGGCATCAGA AGGCTCCGTA TGAACGGAAC AATCTGTTGG GTTTGATCTT      60
GCAGGTTTGT CATGATATCG                                                 80
```

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
GACCTTGAGT GAGTCGACGG TAC                                             23
```

5,891,442

19

20

-continued ( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
CGTCGACTCA CTCAAG                                                                16
```

( 2 ) INFORMATION FOR SEQ ID NO:7:

( i ) SEQUENCE CHARACTERISTICS:
        ( A ) LENGTH: 3661 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
GATATCTGTG  GTCTATATAT  ACTACACCCT  ACCGATATTA  ACCAACGAGT  TTCTCACAAG      60
AAAACTTGTT  TAGTAGATAG  AGATTCTTTG  ATTGTGTTTA  AAAGAAGTAC  CAGTAAAAAG     120
TGTGGCATAT  GCATAGAAGA  AATAAACAAA  AAACATATTT  CCGAACAGTA  TTTTGGAATT     180
CTCCCAAGTT  GTAAACATAT  TTTTTGCCTA  TCATGTATAA  GACGTTGGGC  AGATACTACC     240
AGAAATACAG  ATACTGAAAA  TACGTGTCCT  GAATGTAGAA  TAGTTTTTCC  TTTCATAATA     300
CCCAGTAGGT  ATTGGATAGA  TAATAAATAT  GATAAAAAAA  TATTATATAA  TAGATATAAG     360
AAAATGATTT  TTACAAAAAT  AACCTATAAG  AACAATAAAA  ATATAATTAC  ATTTACGGAA     420
AATAGCTGGT  TTTAGTTTAC  CAACTTAGAG  TAATTATCAT  ATTGAATCTA  TATTGTTTTT     480
TAGTTATATA  AAAACATGAT  TAGCCCCCAA  TCGGATGAAA  ATATAAAAGA  TGTTGAGAAT     540
TTCGAATACA  ACAAAAAGAG  GAATCGTACG  TTGTCCATAT  CCAAACATAT  AAATAAAAAT     600
TCAAAAGTAG  TATTATACTG  GATGTTTAGA  GATCAACGTG  TACAAGATAA  TTGGGCTTTA     660
ATTTACGCAC  AACGATTAGC  GTTAAAACTC  AAAATACCTC  TAAGAATATG  CTTTTGTGTC     720
GTGCCAAAAT  TTCACACTAC  TACTTCTAGT  ACACTTTATG  TTTTTAATAT  CCGGTCTTAA     780
AGAAGTCGCG  GAAGAATGTA  AAAGACTATG  TATAGGGTTT  TCATTGATAT  ATGGCGTACC     840
AAAAGTAATA  ATTCCGTGTA  TAGTAAAAAA  ATACAGAGTC  GGAGTAATCA  TAACGGATTT     900
CTTTCCATTA  CGTGTTCCCG  AAAGATTAAT  GAAACAGACT  GTAATATCTC  TTCCAGATAA     960
CATACCTTTT  ATACAAGTAG  ACGCTCATAA  TATAGTACCT  TGTTGGGAAG  CTTCTGATAA    1020
AGAAGAATAC  GGTGCACGAA  CTTTAAGAAA  AAAGATATTT  GATAAATTAT  ATGAATATAT    1080
GACAGAATTT  CCTGTTGTTC  GTAAACATCC  ATACGGTCCA  TTTTCTATAT  CTATTGCAAA    1140
ACCCAAAAAT  ATATCATTAG  ACAAGACGGT  ATTACCCGTA  AAATGGGCAA  CGCCTGGAAC    1200
AAAAGCTGGA  ATAATTGTTT  TAAAGAATT   TATAAAAAAC  AGATTACCGT  CATACGACGC    1260
GGATCATAAC  AATCCTACGT  GTGACGCTTT  GAGTAACTTA  TCTCCGTGGC  TACATTTTGG    1320
TCATGTATCC  GCACAACGTG  TTGCCTTAGA  AGTATTAAAA  TGTATACGAG  AAAGCAAAAA    1380
AAACGTTGAA  ACGTTTATAG  ATGAAATAAT  TGTAAGAAGA  GAACTATCGG  ATAATTTTTG    1440
TTACTATAAC  AAACATTATG  ATAGTATCCA  GTCTACTCAT  TCATGGGTTA  GAAAAACATT    1500
AGAAGATCAC  ATTAATGATC  CTAGAAAGTA  TATATATTCC  ATTAAACAAC  TCGAAAAAGC    1560
GGAAACTCAT  GATCCTCTAT  GGAACGCGTC  ACAAATGCAG  ATGGTGAGAG  AAGGAAAAAT    1620
GCATAGTTTT  TTACGAATGT  ATTGGGCTAA  GAAGATACTT  GAATGGACTA  GAACACCTGA    1680
```

-continued

| | | | | | | |
|---|---|---|---|---|---|---|
| AGACGCTTTG | AGTTATAGTA | TCTATTTGAA | CAACAAGTAC | GAACTAGACG | GCACGGATCC | 1740 |
| TAACGGATAC | GTAGGTTGTA | TGTGGTCTAT | TTGCGGATTA | CACGATAGAG | CGTGGAAAGC | 1800 |
| AAGACCGATA | TTTGGAAAGA | TAAGATATAT | GAATTATGAG | AGTTCTAAGA | AGAAATTTGA | 1860 |
| TGTTGCTGTA | TTTATACAGA | AATACAATTA | AGATAAATAA | TATACAGCAT | TGTAACCATC | 1920 |
| GTCATCCGTT | ATACGGGAA | TAATATTACC | ATACAGTATT | ATTAAATTTT | CTTACGAAGA | 1980 |
| ATATAGATCG | GTATTTATCG | TTAGTTTATT | TTACATTTAT | TAATTAAACA | TGTCTACTAT | 2040 |
| TACCTGTTAT | GGAAATGACA | AATTTAGTTA | TATAATTTAT | GATAAAATTA | AGATAATAAT | 2100 |
| AATGAAATCA | AATAATTATG | TAAATGCTAC | TAGATTATGT | GAATTACGAG | GAAGAAAGTT | 2160 |
| TACGAACTGG | AAAAAATTAA | GTGAATCTAA | AATATTAGTC | GATAATGTAA | AAAAAATAAA | 2220 |
| TGATAAAACT | AACCAGTTAA | AAACGGATAT | GATTATATAC | GTTAAGGATA | TTGATCATAA | 2280 |
| AGGAAGAGAT | ACTTGCGGTT | ACTATGTACA | CCAAGATCTG | GTATCTTCTA | TATCAAATTG | 2340 |
| GATATCTCCG | TTATTCGCCG | TTAAGGTAAA | TAAAATTATT | AACTATTATA | TATGTAATGA | 2400 |
| ATATGATATA | CGACTTAGCG | AAATGGAATC | TGATATGACA | GAAGTAATAG | ATGTAGTTGA | 2460 |
| TAAATTAGTA | GGAGGATACA | ATGATGAAAT | AGCAGAAATA | ATATATTTGT | TTAATAAATT | 2520 |
| TATAGAAAAA | TATATTGCTA | ACATATCGTT | ATCAACTGAA | TTATCTAGTA | TATTAAATAA | 2580 |
| TTTTATAAAT | TTTATAAATT | TTAATAAAAA | ATACAATAAC | GACATAAAGA | TATTTAATCT | 2640 |
| TTAATTCTTG | ATCTGAAAAA | CACATCTATA | AAACTAGATA | AAAGTTATT | CGATAAAGAT | 2700 |
| AATAATGAAT | CGAACGATGA | AAAATTGGAA | ACAGAAGTTG | ATAAGCTAAT | TTTTTTCATC | 2760 |
| TAAATAGTAT | TATTTATTG | AAGTACGAAG | TTTTACGTTA | GATAAATAAT | AAAGGTCGAT | 2820 |
| TTTTACTTTG | TTAAATATCA | AATATGTCAT | TATCTGATAA | AGATACAAAA | ACACACGGTG | 2880 |
| ATTATCAACC | ATCTAACGAA | CAGATATTAC | AAAAAATACG | TCGGACTATG | GAAAACGAAG | 2940 |
| CTGATAGCCT | CAATAGAAGA | AGCATTAAAG | AAATTGTTGT | AGATGTTATG | AAGAATTGGG | 3000 |
| ATCATCCTCA | ACGAAGAAAT | AGATAAAGTT | CTAAACTGGA | AAAATGATAC | ATTAAACGAT | 3060 |
| TTAGATCATC | TAAATACAGA | TGATAATATT | AAGGAAATCA | TACAATGTCT | GATTAGAGAA | 3120 |
| TTTGCGTTTA | AAAAGATCAA | TTCTATTATG | TATAGTTATG | CTATGGTAAA | ACTCAATTCA | 3180 |
| GATAACGAAC | ATTGAAAGAT | AAAATTAAGG | ATTATTTTAT | AGAAACTATT | CTTAAAGACA | 3240 |
| AACGTGGTTA | TAAACAAAAG | CCATTACCCG | GATTGGAAAC | TAAAATACTA | GATAGTATTA | 3300 |
| TAAGATTTTA | AAAACATAAA | ATTAATAGGT | TTTTATAGAT | TGACTTATTA | TATACAATAT | 3360 |
| GGATAAAAGA | TATATATCAA | CTAGAAAGTT | GAATGACGGA | TTCTTAATTT | TATATTATGA | 3420 |
| TTCAATAGAA | ATTATTGTCA | TGTCGTGTAA | TCATTTATA | AATATATCAG | CGTTACTAGC | 3480 |
| TAAGAAAAAC | AAGGACTTTA | ATGAATGGCT | AAAGATAGAA | TCATTTAGAG | AAATAATAGA | 3540 |
| TACTTTAGAT | AAAATTAATT | ACGATCTAGG | ACAACGATAT | TGTGAAGAAC | TTACGGCGCA | 3600 |
| TCACATTCCA | GTGTAATTAT | TGAGGTCAAA | GCTAGTAACT | TAATAGATGA | CAGGACAGCT | 3660 |
| G | | | | | | 3661 |

( 2 ) INFORMATION FOR SEQ ID NO:8:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

| | | | | | | |
|---|---|---|---|---|---|---|
| CTAGACACTT | TATGTTTTTT | AATATCCGGT | CTTAAAAGCT | TCCCGGGGGA | TCCTTATACG | 60 |

GGGAATAAT 69

( 2 ) INFORMATION FOR SEQ ID NO:9:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
ATTATTCCCC GTATAAGGAT CCCCCGGGAA GCTTTTAAGA CCGGATATTA AAAAACATAA      60
AGTGT                                                                  65
```

( 2 ) INFORMATION FOR SEQ ID NO:10:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GATCAGAAAA ACTAGCTAGC TAGTACGTAG TTAACGTCGA CCTGCAGAAG CTTCTAGCTA      60
GCTAGTTTTT AT                                                          72
```

( 2 ) INFORMATION FOR SEQ ID NO:11:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
AGCTATAAAA ACTAGCTAGC TAGAAGCTTC TGCAGGTCGA CGTTAACTAC GTACTAGCTA      60
GCTAGTTTTT CT                                                          72
```

( 2 ) INFORMATION FOR SEQ ID NO:12:

( i ) SEQUENCE CHARACTERISTICS:
        ( A ) LENGTH: 3659 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
GATATCTGTG GTCTATATAT ACTACACCCT ACCGATATTA ACCAACGAGT TTCTCACAAG      60
AAAACTTGTT TAGTAGATAG AGATTCTTTG ATTGTGTTTA AAAGAAGTAC CAGTAAAAAG     120
TGTGGCATAT GCATAGAAGA AATAAACAAA AAACATATTT CCGAACAGTA TTTTGGAATT     180
CTCCCAAGTT GTAAACATAT TTTTTGCCTA TCATGTATAA GACGTTGGGC AGATACTACC     240
AGAAATACAG ATACTGAAAA TACGTGTCCT GAATGTAGAA TAGTTTTTCC TTTCATAATA     300
CCCAGTAGGT ATTGGATAGA TAATAAATAT GATAAAAAAA TATTATATAA TAGATATAAG     360
AAAATGATTT TTACAAAAAT ACCTATAAGA ACAATAAAAA TATAATTACA TTTACGGAAA     420
ATAGCTGGTT TTAGTTTACC AACTTAGAGT AATTATCATA TTGAATCTAT ATTGTTTTTT     480
AGTTATATAA AAACATGATT AGCCCCCAAT CGGATGAAAA TATAAAGAT GTTGAGAATT      540
TCGAATACAA CAAAAGAGG AATCGTACGT TGTCCATATC CAAACATATA AATAAAAATT      600
CAAAAGTAGT ATTATACTGG ATGTTTAGAG ATCAACGTGT ACAAGATAAT TGGGCTTTAA     660
```

```
TTTACGCACA  ACGATTAGCG  TTAAAACTCA  AAATACCTCT  AAGAATATGC  TTTTGTGTCG   720
TGCCAAAATT  TCACACTACT  ACTTCTAGAC  ACTTTATGTT  TTTAATATCC  GGTCTTAAAG   780
AAGTCGCGGA  AGAATGTAAA  AGACTATGTA  TAGGGTTTTC  ATTGATATAT  GGCGTACCAA   840
AAGTAATAAT  TCCGTGTATA  GTAAAAAAAT  ACAGAGTCGG  AGTAATCATA  ACGGATTTCT   900
TTCCATTACG  TGTTCCCGAA  AGATTAATGA  AACAGACTGT  AATATCTCTT  CCAGATAACA   960
TACCTTTTAT  ACAAGTAGAC  GCTCATAATA  TAGTACCTTG  TTGGGAAGCT  TCTGATAAAG  1020
AAGAATACGG  TGCACGAACT  TTAAGAAAAA  AGATATTTGA  TAAATTATAT  GAATATATGA  1080
CAGAATTTCC  TGTTGTTCGT  AAACATCCAT  ACGGTCCATT  TTCTATATCT  ATTGCAAAAC  1140
CCAAAAATAT  ATCATTAGAC  AAGACGGTAT  TACCCGTAAA  ATGGGCAACG  CCTGGAACAA  1200
AAGCTGGAAT  AATTGTTTTA  AAAGAATTTA  TAAAAAACAG  ATTACCGTCA  TACGACGCGG  1260
ATCATAACAA  TCCTACGTGT  GACGCTTTGA  GTAACTTATC  TCCGTGGCTA  CATTTGGTC  1320
ATGTATCCGC  ACAACGTGTT  GCCTTAGAAG  TATTAAAATG  TATACGAGAA  AGCAAAAAAA  1380
ACGTTGAAAC  GTTTATAGAT  GAAATAATTG  TAAGAAGAGA  ACTATCGGAT  AATTTTTGTT  1440
ACTATAACAA  ACATTATGAT  AGTATCCAGT  CTACTCATTC  ATGGGTTAGA  AAAACATTAG  1500
AAGATCACAT  TAATGATCCT  AGAAAGTATA  TATATTCCAT  TAAACAACTC  GAAAAAGCGG  1560
AAACTCATGA  TCCTCTATGG  AACGCGTCAC  AAATGCAGAT  GGTGAGAGAA  GGAAAAATGC  1620
ATAGTTTTTT  ACGAATGTAT  TGGGCTAAGA  AGATACTTGA  ATGGACTAGA  ACACCTGAAG  1680
ACGCTTTGAG  TTATAGTATC  TATTTGAACA  ACAAGTACGA  ACTAGACGGC  ACGGATCCTA  1740
ACGGATACGT  AGGTTGTATG  TGGTCTATTT  GCGGATTACA  CGATAGAGCG  TGGAAAGCAA  1800
GACCGATATT  TGGAAAGATA  AGATATATGA  ATTATGAGAG  TTCTAAGAAG  AAATTTGATG  1860
TTGCTGTATT  TATACAGAAA  TACAATTAAG  ATAAATAATA  TACAGCATTG  TAACCATCGT  1920
CATCCGTTAT  ACGGGGAATA  ATATTACCAT  ACAGTATTAT  TAAATTTTCT  TACGAAGAAT  1980
ATAGATCGGT  ATTTATCGTT  AGTTTATTTT  ACATTTATTA  ATTAAACATG  TCTACTATTA  2040
CCTGTTATGG  AAATGACAAA  TTTAGTTATA  TAATTTATGA  TAAAATTAAG  ATAATAATAA  2100
TGAAATCAAA  TAATTATGTA  AATGCTACTA  GATTATGTGA  ATTACGAGGA  AGAAAGTTTA  2160
CGAACTGGAA  AAAATTAAGT  GAATCTAAAA  TATTAGTCGA  TAATGTAAAA  AAAATAAATG  2220
ATAAAACTAA  CCAGTTAAAA  ACGGATATGA  TTATATACGT  TAAGGATATT  GATCATAAAG  2280
GAAGAGATAC  TTGCGGTTAC  TATGTACACC  AAGATCTGGT  ATCTTCTATA  TCAAATTGGA  2340
TATCTCCGTT  ATTCGCCGTT  AAGGTAAATA  AAATTATTAA  CTATTATATA  TGTAATGAAT  2400
ATGATATACG  ACTTAGCGAA  ATGGAATCTG  ATATGACAGA  AGTAATAGAT  GTAGTTGATA  2460
AATTAGTAGG  AGGATACAAT  GATGAAATAG  CAGAAATAAT  ATATTTGTTT  AATAAATTTA  2520
TAGAAAAATA  TATTGCTAAC  ATATCGTTAT  CAACTGAATT  ATCTAGTATA  TTAAATAATT  2580
TTATAAATTT  TATAAATTTT  AATAAAAAAT  ACAATAACGA  CATAAAGATA  TTTAATCTTT  2640
AATTCTTGAT  CTGAAAAACA  CATCTATAAA  ACTAGATAAA  AAGTTATTCG  ATAAAGATAA  2700
TAATGAATCG  AACGATGAAA  AATTGGAAAC  AGAAGTTGAT  AAGCTAATTT  TTTTCATCTA  2760
AATAGTATTA  TTTTATTGAA  GTACGAAGTT  TTACGTTAGA  TAAATAATAA  AGGTCGATTT  2820
TTACTTTGTT  AAATATCAAA  TATGTCATTA  TCTGATAAAG  ATACAAAAAC  ACACGGTGAT  2880
TATCAACCAT  CTAACGAACA  GATATTACAA  AAAATACGTC  GGACTATGGA  AAACGAAGCT  2940
GATAGCCTCA  ATAGAAGAAG  CATTAAAGAA  ATTGTTGTAG  ATGTTATGAA  GAATTGGGAT  3000
CATCCTCAAC  GAAGAAATAG  ATAAAGTTCT  AAACTGGAAA  AATGATACAT  TAAACGATTT  3060
```

```
AGATCATCTA  AATACAGATG  ATAATATTAA  GGAAATCATA  CAATGTCTGA  TTAGAGAATT        3120

TGCGTTTAAA  AAGATCAATT  CTATTATGTA  TAGTTATGCT  ATGGTAAAAC  TCAATTCAGA        3180

TAACGAACAT  TGAAAGATAA  AATTAAGGAT  TATTTTATAG  AAACTATTCT  TAAAGACAAA        3240

CGTGGTTATA  AACAAAGCC   ATTACCCGGA  TTGGAAACTA  AAATACTAGA  TAGTATTATA        3300

AGATTTTAAA  AACATAAAAT  TAATAGGTTT  TTATAGATTG  ACTTATTATA  TACAATATGG        3360

ATAAAGATA   TATATCAACT  AGAAGTTGA   ATGACGGATT  CTTAATTTTA  TATTATGATT        3420

CAATAGAAAT  TATTGTCATG  TCGTGTAATC  ATTTTATAAA  TATATCAGCG  TTACTAGCTA        3480

AGAAAAACAA  GGACTTTAAT  GAATGGCTAA  AGATAGAATC  ATTTAGAGAA  ATAATAGATA        3540

CTTTAGATAA  AATTAATTAC  GATCTAGGAC  AACGATATTG  TGAAGAACTT  ACGGCGCATC        3600

ACATTCCAGT  GTAATTATTG  AGGTCAAAGC  TAGTAACTTA  ATAGATGACA  GGACAGCTG        3659
```

(2) INFORMATION FOR SEQ ID NO:13:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:13:

```
AATTAACCCG  GGATCCAAGC  TTCTAGCTAG  CTAATTTTTA  TAGCGGCCGC  TATAATCGTT        60

AACTTATTAG                                                                    70
```

(2) INFORMATION FOR SEQ ID NO:14:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (xi) SEQUENCE DESCRIPTION: SEQ ID NO:14:

```
CTAGCTAGAA  GCTTGGATCC  CGGGTTAATT  AATTAATAAA  AAGCGGCCGC  GTTAAAGTAG        60

AAAAATG                                                                       67
```

(2) INFORMATION FOR SEQ ID NO:15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:15:

```
GTTACATATG  TACAGAATCT  GATCATAG                                              28
```

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:16:

```
GCTAGAATTC  TCTTAGTTTT  TATAGTTG                                              28
```

(2) INFORMATION FOR SEQ ID NO:17:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:17:

AAGGTAGTAC TGGCGTCC                                                                                  18

( 2 ) INFORMATION FOR SEQ ID NO:18:

( i ) SEQUENCE CHARACTERISTICS:
                ( A ) LENGTH: 54 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:18:

TTATCGCGAT ATCCGTTAAG TTTGTATCGT AATATGTTCC CTCACAATCC ACGA                                           54

( 2 ) INFORMATION FOR SEQ ID NO:19:

( i ) SEQUENCE CHARACTERISTICS:
                ( A ) LENGTH: 26 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:19:

TAAAAGCTTT TAATTAATTA GTCATC                                                                         26

( 2 ) INFORMATION FOR SEQ ID NO:20:

( i ) SEQUENCE CHARACTERISTICS:
                ( A ) LENGTH: 26 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:20:

TAACCCGGGC GATACAAACT TAACGG                                                                         26

( 2 ) INFORMATION FOR SEQ ID NO:21:

( i ) SEQUENCE CHARACTERISTICS:
                ( A ) LENGTH: 72 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:21:

GATCCCGGTA CCTCTAATGC TGATCATCCG AACCGCGCTG ACACTGAGCT GTACAAACCT                                     60

GCAAGATCAA AC                                                                                        72

( 2 ) INFORMATION FOR SEQ ID NO:22:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:22:

GGACGCCGGT CCGGTTGTTG GCATC                                                                          25

( 2 ) INFORMATION FOR SEQ ID NO:23:

( i ) SEQUENCE CHARACTERISTICS:
 ( A ) LENGTH: 112 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:23:

GTGAGTACTT CATGGAGGTG GCCGACCTCA ACTCTCCCT GAAGATTGCA GGAGCATTTG    60

GCTTCAAAGA CATAATCCGG GCTATAAGGA GGATCGTTTT AACTGTCATA TC    112

( 2 ) INFORMATION FOR SEQ ID NO:24:

( i ) SEQUENCE CHARACTERISTICS:
  ( A ) LENGTH: 31 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:24:

TTAGGATCCT CATATTTTTG TAGTGGCTCT C    31

( 2 ) INFORMATION FOR SEQ ID NO:25:

( i ) SEQUENCE CHARACTERISTICS:
  ( A ) LENGTH: 42 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:25:

TACACACTGC AGAGCAATGG GAACCTCAAG TTCGATCAGA TG    42

( 2 ) INFORMATION FOR SEQ ID NO:26:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:26:

GAAACACGAG CTCTCCCCCA ACGCTGAGGC TTGTGATAG    39

( 2 ) INFORMATION FOR SEQ ID NO:27:

( i ) SEQUENCE CHARACTERISTICS:
  ( A ) LENGTH: 155 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:27:

GGAAGAGCTC GTGTTTCAAA CAAGCGTCCA AGGCCTTGTA CTGGGCGCCA CCATCTACTT    60

TATAGGCTTT GATGGGACTA CGGTAATCAC CAGAGCTGTA GCCGCAGATA ATGGGCTGAC    120

GGCCGGCACC GACAATCTTA TGCCATTCAA TCTTG    155

( 2 ) INFORMATION FOR SEQ ID NO:28:

( i ) SEQUENCE CHARACTERISTICS:
  ( A ) LENGTH: 155 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:28:

CCACCATGGA TCGTCACTGC TAGGCTCCCA CTTGCCGACC ATGACATCTG ATCCCCTGCC    60

TGACCACCAC TTTTGGAGGT CACTACCTCC AGTTTGATGG ATGTGATTGG CTGGGTTATC    120

TCATTGGTTG GAATGACAAG ATTGAATGGC ATAAG    155

( 2 ) INFORMATION FOR SEQ ID NO:29:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

GGGAGAGCTC GTGTTTCAAA CAAGCG    26

( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

CCACCATGGA TCGTCACTGC    20

( 2 ) INFORMATION FOR SEQ ID NO:31:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

AACATATTTC CGAACAG    17

( 2 ) INFORMATION FOR SEQ ID NO:32:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

TCCAAGCTTT CGCGACCCGG GTTTTTATTA GCTAATTAGC AATATAGATT CAATATG    57

( 2 ) INFORMATION FOR SEQ ID NO:33:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

ATCAAGCTTG GATCCCTCGA GTTTTTATTG ACTAGTTAAT CATAAGATAA ATAATATACA    60

GC    62

( 2 ) INFORMATION FOR SEQ ID NO:34:

( i ) SEQUENCE CHARACTERISTICS:
        ( A ) LENGTH: 17 base pairs
        ( B ) TYPE: nucleic acid -continued (C) STRANDEDNESS: single
(D) TOPOLOGY: linear (xi) SEQUENCE DESCRIPTION: SEQ ID NO:34:

GATATAGAAG ATACCAG                                    17

REFERENCES

1. Allan, W. H., J. T. Faragher, and G. A. Cullen, Vet. Rec. 90, 511–512 (1972).
2. Azad, A. A., S. A. Barrett, and K. J. Fahey, Virology 143, 35–44 (1985).
3. Azad, A. A., K. J. Fahey, S. Barrett, K. Erny and P. Hudson, Virology 149, 190–198 (1986).
4. Azad, A. A., M. N. Jagadish, M. A. Brown, and P. J. Hudson, Virology 161, 145–152 (1987).
5. Baxendale, W. and Lutticken, Dev. Biol. Stand. 51, 211–219 (1981).
6. Bayliss, C. D., U. Spies, K. Shaw, R. W. Peters, A. Papageorgiou, H. Muller, and M. E. G. Boursnell, J. Gen. Virol. 71, 1303–1312 (1990).
7. Becht, H., H. Muller, and H. K. Muller, J. Gen. Virol. 69, 631–640 (1988).
8. Bertholet, C., R. Drillien, and R. Wittek, Proc. Natl. Acad. Sci. U.S.A. 82, 2096–2100 (1985).
9. Brown, F., Intervirology 25, 141–143 (1986).
10. Burkhardt, E. and H. Muller, Archives of Virology 94, 297–303 (1987).
11. Casadaban, M. J., A. Martinez-Arias, S. K. Shapira and J. Chou, Methods in Enzymol. 100, 293–307 (1983).
12. Clewell, D. B., J. Bacteriol. 110, 667–676 (1972).
13. Clewell, D. B. and D. R. Helinski, Proc. Natl. Acad. Sci. USA 62, 1159–1166 (1969).
14. Dobos, P., J. Virol. 32, 1046–1050 (1979).
15. Dobos, P., B. J. Hill, R. Hallett, D. T. Kells, H. Becht, and D. Teninges, J. Virol. 32, 593–605 (1979).
16. Duncan, R., E. Nagy, P. J. Krell and P. Dobos, J. Virol. 61, 3655–3664 (1987).
17. Edbauer, C., R. Weinberg, J. Taylor, A. Rey-Senelonge, J. F. Bouquet, P. Desmettre and E. Paoletti, Virology 179, 901–904 (1990).
18. Fahey, K. J., I. J. O'Donnell, and A. A. Azad, J. Gen. Virol. 66, 1479–1488 (1985a).
19. Fahey, K. J., I. J. O'Donnell, and T. J. Bagust, J. Gen. Virol. 66, 2693–2702 (1985 b).
20. Fahey, K. J., K. Erny and J. Crooks, J. Gen. Virol. 70, 1473–1481 (1989).
21. Guo, P., S. Goebel, S. Davis, M. E. Perkus, B. Languet, P. Desmettre, G. Allen, and E. Paoletti, J. Virol. 63, 4189–4198 (1989).
22. Hudson, P. J., N. M. McKern, B. E. Power, and A. A. Azad, Nucl. Acids. Res. 14, 5001–5012 (1986).
23. Jackwood, D. J., Y. M. Saif, and J. H. Hughes, Avian Dis. 28, 990–1006 (1984).
24. Jagadish, M. N., V. J. Staton, P. J. Hudson, and A. A. Azad, J. Virol. 62, 1084–1087 (1988).
25. Kaufer, I. and E. Weiss, Infect. Immun. 27, 364–367 (1980).
26. Kibenge, F. S. B., A. S. Dhillon, and R. G. Russell, J. Gen. Virol. 69, 1757–1775 (1988).
27. Kibenge, F. S. B., D. J. Jackwood, and C. C. Mercado, J. Gen. Virol. 71, 569–577 (1990).
28. Langford, C. J., S. J. Edwards, G. L. Smith, G. F. Mitchell, B. Moss, D. J. Kemp, and R. F. Anders, Mol. Cell. Biol. 6, 3191–3199 (1986).
29. Ley, D. H., R. Yamamoto, and A. A. Bickford, Avian Diseases 23, 219–224 (1979).
30. Lucio, B. and S. B. Hitchner, Avian Dis. 23, 466–478 (1979).
31. Lukert, P. D. and S. B. Hitchner, In Diseases of Poultry 8th edition, eds. M. S. Hofstad, H. J. Barnes, B. W. Calnek, W. M. Reid and H. W. Yoder (Iowa State University Press-Ames) pp. 566–576 (1984).
32. Lukert, P. D. and L. A. Mazariegos, J. Am. Vet. Med. Assoc. 187, 306 (ABSTR) (1985).
33. Lukert, P. D. and Y. M. Saif, In Diseases of Poultry 9th edition, eds. B. W. Calnek, H. J. Barnes, C. W. Beard, W. M. Reid and H. W. Yoder (Iowa State University Press-Ames) pp. 648–663 (1991).
34. Macreadie, I. G., P. R. Vaughan, A. J. Chapman, N. M. McKern, M. N. Jagadish, H. G. Heine, C. W. Ward, K. J. Fahey, and A. A. Azad, Vaccine 8, 549–552 (1990).
35. Matthews, R. E. F., Intervirology 17, 42–44 (1982).
36. McFerran, J. B., M. S. McNulty, E. R. McKillop, T. J. Connor, R. M. McCracken, D. S. Collins, and G. M. Allen, Avian Pathol. 9, 395–404 (1980). p0 37. McNulty, M. S. and Y. M. Saif, Avian Dis. 32, 374–375 (1988).
38. Muller, H., Arch. Virol. 87, 191–203 (i986).
39. Muller, H. and H. Betch, J. Virol. 44, 384–392 (1982).
40. Nagy, E., R. Duncan, P. Krell, and P. Dobos, Virology 158, 211–217 (1987).
41. Panicali, D. and E. Paoletti, Proc. Natl. Acad. Sci. USA 79, 4927–4931 (1982).
42. Paoletti, E., B. R. Lipinskaks, C. Samsonoff, S. Mercer, and D. Panicali, Proc. Natl. Acad. Sci. U.S.A. 81, 193–197 (1984).
43. Perkus, M. E., K. Limbach, and E. Paoletti, J. Virol. 63, 3829–3836 (1989).
44. Piccini, A., M. E. Perkus, and E. Paoletti, In Methods in Enzymology, Vol. 153, eds. Wu, R., and Grossman, L., (Academic Press) pp. 545–563 (1987).
45. Sambrook, J., E. F. Fritsch, and T. Maniatis, In Molecular cloning: A laboratory manual, 2nd edition, (Cold Spring Harbor Press, NY) (1989).
46. Schat, K. A., B. Lucio, and J. C. Carlisle, Avian Dis. 25, 996–1004 (1981).
47. Shapira, S. K., J. Chou, F. V. Richaud, and M. J. Casadaban, Gene 25, 71–82 (1983).
48. Skeeles, J. K., P. D. Lukert, E. V. De Buysscher, O. J. Fletcher, and J. Brown, Avian Dis. 23, 95–106 (1979).
49. Snyder, D. B., D. P Lana, B. R. Cho, and W. W. Marquardt, Avian Dis. 32, 527–534 (1988).
50. Spies, U., H. Muller, and H. Becht, Virus Res. 8, 127–140 (1987).
51. Tartaglia, J., J. Winslow, S. Goebel, G. P. Johnson, J. Taylor, and E. Paoletti, J. Gen. Virol. 71, 1517–1524 (1990).
52. Taylor, J., R. Weinberg, Y. Kawaoka, R. Webster and E. Paoletti, Vaccine 6, 504–508 (1988).
53. Taylor, J., C. Edbauer, A. Rey-Senelonge, J. F. Bouquet, E. Norton, S. Goebel, P. Desmettre and E. Paoletti, J. Virol. 64, 1441–1450 (1990).
54. Vijaya, S., N. Elango, F. Zavala, and B. Moss, Mol. Cell. Biol. 8, 1709–1714 (1988).

55. Winterfield, R. W., A. M. Fadly, and A. Bickford. Avian Dis. 16, 622–632 (1972).
56. Winterfield, R. W., A. S. Dhillon, H. L. Thacker, L. J. Alby, Avian Dis. 24, 179–188 (1980).

What is claimed is:

1. A recombinant avipox virus comprising DNA from infectious bursal disease virus which codes for and is expressed as an infectious bursal disease virus structural protein VP2 or polyprotein VP2, VP3, VP4, wherein the recombinant avipox virus induces an immunological response in a host animal inoculated therewith.

2. A TROVAC recombinant poxvirus or a poxvirus having all of the identifying characteristics of TROVAC comprising exogenous DNA from infectious bursal disease virus.

3. The recombinant avipox virus of claim 1 which is a fowlpox virus.

4. The recombinant avipox virus of claim 3 which is a TROVAC fowlpox virus or a poxvirus having all of the identifying characteristics of TROVAC.

5. The recombinant avipox virus of claim 4 wherein the DNA from infectious bursal disease virus codes for and is expressed as infectious bursal disease virus structural protein VP2.

6. The recombinant avipox virus of claim 4 which is vFP115 or vFP116.

7. The recombinant avipox virus of claim 1 which is a fowlpox virus which has attenuated virulence through approximately 50 serial passages on chicken embryo firbroblast cells, then subjecting the fowlpox virus to four successive plaque purifications, and obtaining a plaque isolate and further amplifying the isolate in primary chick embryo fibroblast cells.

8. The recombinant avipox virus of claim 4 wherein the DNA from infectious bursal disease virus codes for and is expressed as infectious bursal disease virus structural polyprotein VP2, VP3, VP4.

9. An immunological composition for inducing an immunological response in a host inoculated with the immunological composition, said immmunological composition comprising a carrier and the recombinant avipox virus of claim 1.

10. An immunological composition for inducing an immunological response in a host inoculated with the immunological composition, said immmunological composition comprising a carrier and the recombinant avipox virus of claim 2.

11. An immunological composition for inducing an immunological response in a host inoculated with the immunological composition, said immmunological composition comprising a carrier and the recombinant avipox virus of claim 3.

12. An immunological composition for inducing an immunological response in a host inoculated with the immunological composition, said immmunological composition comprising a carrier and the recombinant avipox virus of claim 5.

13. An immunological composition for inducing an immunological response in a host inoculated with the immunological composition, said immmunological composition comprising a carrier and the recombinant avipox virus of claim 4.

14. An immunological composition for inducing an immunological response in a host inoculated with the immunological composition, said immmunological composition comprising a carrier and the recombinant avipox virus of claim 6.

15. An immunological composition for inducing an immunological response in a host inoculated with the immunological composition, said immmunological composition comprising a carrier and the recombinant avipox virus of claim 7.

16. An immunological composition for inducing an immunological response in a host inoculated with the immunological composition, said immmunological composition comprising a carrier and the recombinant avipox virus of claim 8.

17. A method for inducing an immunological response in a host comprising administering to the host the immunological composition of claim 9.

18. A method for inducing an immunological response in a host comprising administering to the host the immunological composition of claim 10.

19. A method for inducing an immunological response in a host comprising administering to the host the immunological composition of claim 11.

20. A method for inducing an immunological response in a host comprising administering to the host the immunological composition of claim 12.

21. A method for inducing an immunological response in a host comprising administering to the host the immunological composition of claim 13.

22. A method for inducing an immunological response in a host comprising administering to the host the immunological composition of claim 14.

23. A method for inducing an immunological response in a host comprising administering to the host the immunological composition of claim 15.

24. A method for inducing an immunological response in a host comprising administering to the host the immunological composition of claim 16.

25. The method of claim 17 wherein the host is a chicken.
26. The method of claim 18 wherein the host is a chicken.
27. The method of claim 19 wherein the host is a chicken.
28. The method of claim 20 wherein the host is a chicken.
29. The method of claim 21 wherein the host is a chicken.
30. The method of claim 22 wherein the host is a chicken.
31. The method of claim 23 wherein the host is a chicken.
32. The method of claim 24 wherein the host is a chicken.

33. A method for preparing an infectious bursal disease virus structural protein comprising introducing into cells of an in vitro cell culture a recombinant avipox virus of claim 1 and culturing the cells under conditions allowing expression of the infectious bursal disease virus structural protein by the avipox virus.

34. A method for preparing an infectious bursal disease virus gene product comprising introducing into cells of an in vitro cell culture a recombinant avipox virus of claim 2 and culturing the cells under conditions allowing expression of the infectious bursal disease virus gene product by the avipox virus.

35. A method for preparing an infectious bursal disease virus structural protein comprising introducing into cells of an in vitro cell culture a recombinant avipox virus of claim 3 and culturing the cells under conditions allowing expression of the infectious bursal disease virus structural protein by the avipox virus.

36. A method for preparing an infectious bursal disease virus structural protein comprising introducing into cells of an in vitro cell culture a recombinant avipox virus of claim 5 and culturing the cells under conditions allowing expression of the infectious bursal disease virus structural protein by the avipox virus.

37. A method for preparing an infectious bursal disease virus structural protein comprising introducing into cells of an in vitro cell culture a recombinant avipox virus of claim 4 and culturing the cells under conditions allowing expression of the infectious bursal disease virus structural protein by the avipox virus.

38. A method for preparing an infectious bursal disease virus structural protein comprising introducing into cells of an in vitro cell culture a recombinant avipox virus of claim 6 and culturing the cells under conditions allowing expression of the infectious bursal disease virus structural protein by the avipox virus.

39. A method for preparing an infectious bursal disease virus structural protein comprising introducing into cells of an in vitro cell culture a recombinant avipox virus of claim 7 and culturing the cells under conditions allowing expression of the infectious bursal disease virus structural protein by the avipox virus.

40. A method for preparing an infectious bursal disease virus structural protein comprising introducing into cells of an in vitro cell culture a recombinant avipox virus of claim 8 and culturing the cells under conditions allowing expression of the infectious bursal disease virus structural protein by the avipox virus.

* * * * *